US010881588B2

(12) United States Patent
Gabriel

(10) Patent No.: US 10,881,588 B2
(45) Date of Patent: Jan. 5, 2021

(54) METHODS AND KITS FOR INSERTING A TUBE THROUGH THE NASOPHARYNX OF A PATIENT

(71) Applicant: Syncro Medical Innovations, Inc., Macon, GA (US)

(72) Inventor: Sabry Gabriel, Lizella, GA (US)

(73) Assignee: Syncro Medical Innovations, Inc., Macon, GA (US)

( * ) Notice: Subject to any disclaimer, the term of this patent is extended or adjusted under 35 U.S.C. 154(b) by 424 days.

(21) Appl. No.: 15/848,135

(22) Filed: Dec. 20, 2017

(65) Prior Publication Data

US 2019/0183741 A1 Jun. 20, 2019

(51) Int. Cl.
*A61M 15/00* (2006.01)
*A61J 15/00* (2006.01)

(52) U.S. Cl.
CPC ....... *A61J 15/0003* (2013.01); *A61J 15/0049* (2013.01); *A61J 15/0061* (2013.01); *A61J 15/0069* (2013.01); *A61J 15/0073* (2013.01)

(58) Field of Classification Search
CPC .... A61J 15/00; A61J 15/0003; A61J 15/0007; A61J 15/0015; A61J 15/0019; A61J 15/0026; A61J 15/003; A61J 15/0046; A61J 15/0049; A61J 15/0065; A61J 15/0073; A61J 15/008; A61J 15/0084; A61J 15/0088; A61J 15/0092; A61J 15/0096; A61M 16/0461; A61M 16/0666; A61M 16/0672; A61M 25/0147; A61M 2025/015; A61M 2210/0618
See application file for complete search history.

(56) References Cited

U.S. PATENT DOCUMENTS

| | | | | | |
|---|---|---|---|---|---|
| 3,776,222 | A | * | 12/1973 | Smiddy | A61B 1/0056 600/146 |
| 4,150,676 | A | * | 4/1979 | Jackson | A61M 25/09033 128/207.18 |
| 4,495,948 | A | * | 1/1985 | Shapiro | A61M 16/04 128/207.15 |
| 4,747,827 | A | * | 5/1988 | Micek | A61J 15/0007 604/516 |
| 5,758,656 | A | * | 6/1998 | Schroeder | A61M 25/0147 600/585 |

(Continued)

*Primary Examiner* — Kami A Bosworth
(74) *Attorney, Agent, or Firm* — Withers & Keys, LLC

(57) ABSTRACT

Methods of inserting a tube through the nasopharynx of a patient are disclosed. The methods of inserting a tube through a nasopharynx of a patient includes the steps of inserting the tube through a naris of the patient; and when a distal end of the tube is proximate a rear surface of the nasopharynx, pulling on or holding in place a thread-like member attached to a tube portion of the distal end of the tube so as to alter an initial direction of the distal end of the tube and point the distal end of the tube towards a throat of the patient. Kits for inserting a tube through the nasopharynx of a patient are also disclosed. The kits include a tube sized so as to move through a nasopharynx of a patient; and a thread-like member that is attachable to a tube portion of a distal end of the tube and can be tensioned so as to alter an initial direction of the distal end of the tube and point the distal end of the tube towards a throat of the patient. Methods of making kits for inserting a tube through the nasopharynx of a patient are further disclosed.

15 Claims, 19 Drawing Sheets

(56) References Cited

U.S. PATENT DOCUMENTS

| | | | | |
|---|---|---|---|---|
| 2003/0154986 | A1* | 8/2003 | Fariss | A61J 15/0003<br>128/207.14 |
| 2014/0163528 | A1* | 6/2014 | Heyns | A61M 39/08<br>604/516 |
| 2017/0105904 | A1* | 4/2017 | Tatarek | A61J 15/0003 |

* cited by examiner

METHODS AND KITS FOR INSERTING A TUBE THROUGH THE NASOPHARYNX OF A PATIENT

FIELD OF THE INVENTION

The present invention is directed to methods for inserting a tube through the nasopharynx of a patient. The prevent invention is further directed to kits for inserting a tube through the nasopharynx of a patient. The present invention is even further directed to methods of making kits for inserting a tube through the nasopharynx of a patient.

BACKGROUND

Insertion of a tube, such as a feeding tube, through the nasopharynx of a patient can cause trauma and pain to a patient due to the inflexibility of tubes and contact of an end of the tube with the nasopharynx of a patient. As shown in FIGS. 1A-1B, during insertion of feeding tube 20, a distal end 24 with distal tip 25 of feeding tube 20 comes into contact with rear surface 482 of nasopharynx 481 of patient 480 as feeding tube 20 is advanced towards throat area 483 of patient 480. Such contact with rear surface 482 of nasopharynx 481 by distal end 24 with distal tip 25 of feeding tube 20 can cause trauma and/or bleeding along rear surface 482 of nasopharynx 481.

Efforts continue to further develop methods for inserting a tube through the nasopharynx of a patient so as to reduce and/or eliminate trauma and pain associated with the insertion of a tube through the nasopharynx of the patient.

SUMMARY

The present invention addresses some of the difficulties and problems discussed above by the discovery of new methods and kits for inserting a tube through the nasopharynx of a patient.

Accordingly, the present invention is directed to methods of inserting a tube through the nasopharynx of a patient. In one exemplary embodiment, the method of inserting a tube through the nasopharynx of a patient comprises: inserting the tube through a naris of the patient; and when a distal end of the tube is proximate a rear surface of the nasopharynx, pulling on and/or holding in place a thread-like member attached to a tube portion of the distal end of the tube so as to alter an initial direction of the distal end of the tube and point the distal end of the tube towards a throat of the patient. The method of inserting a tube through the nasopharynx of a patient may further comprise a number of steps including, but not limited to, one or more of: advancing the distal end of the tube toward the throat area of the patient while pulling on and/or holding in place the thread-like member; disengaging the thread-like member from the tube; removing the thread-like member from the patient while the tube remains in the patient; further advancing the distal end of the tube toward the throat area of the patient without the thread-like member; delivering one or more nutrients to the patient through one or more openings or side holes within the tube; and removing the tube from the patient.

The present invention further relates to kits for inserting a tube through the nasopharynx of a patient. In one exemplary embodiment, the kit comprises a tube sized so as to move through the nasopharynx of a patient; and a thread-like member that is attachable to a tube portion of a distal end of the tube and can be tensioned so as to alter an initial direction of the distal end of the tube and point the distal end of the tube towards a throat of the patient. In some embodiments, the tube portion of the distal end of the tube comprises one or more side holes extending through a sidewall of the tube; and the thread-like member comprises thread or string with a length of from about 20 to about 80 centimeters (cm), and a size so as to enable the thread or string to extend through the one or more side holes. In some embodiments, the tube of the kit comprises a feeding tube.

The present invention even further relates to methods of making kits for inserting a tube through the nasopharynx of a patient. In one exemplary embodiment, the method of making a kit comprises: combining any one of the herein-disclosed tubes with a thread-like member that is attachable to a tube portion of a distal end of the tube and can be tensioned so as to alter an initial direction of the distal end of the tube and point the distal end of the tube towards a throat of the patient.

These and other features and advantages of the present invention will become apparent after a review of the following detailed description of the disclosed embodiments and the appended claims.

BRIEF DESCRIPTION OF THE DRAWINGS

The present invention is further described with reference to the appended figures, wherein.

DETAILED DESCRIPTION

Figure 1A:
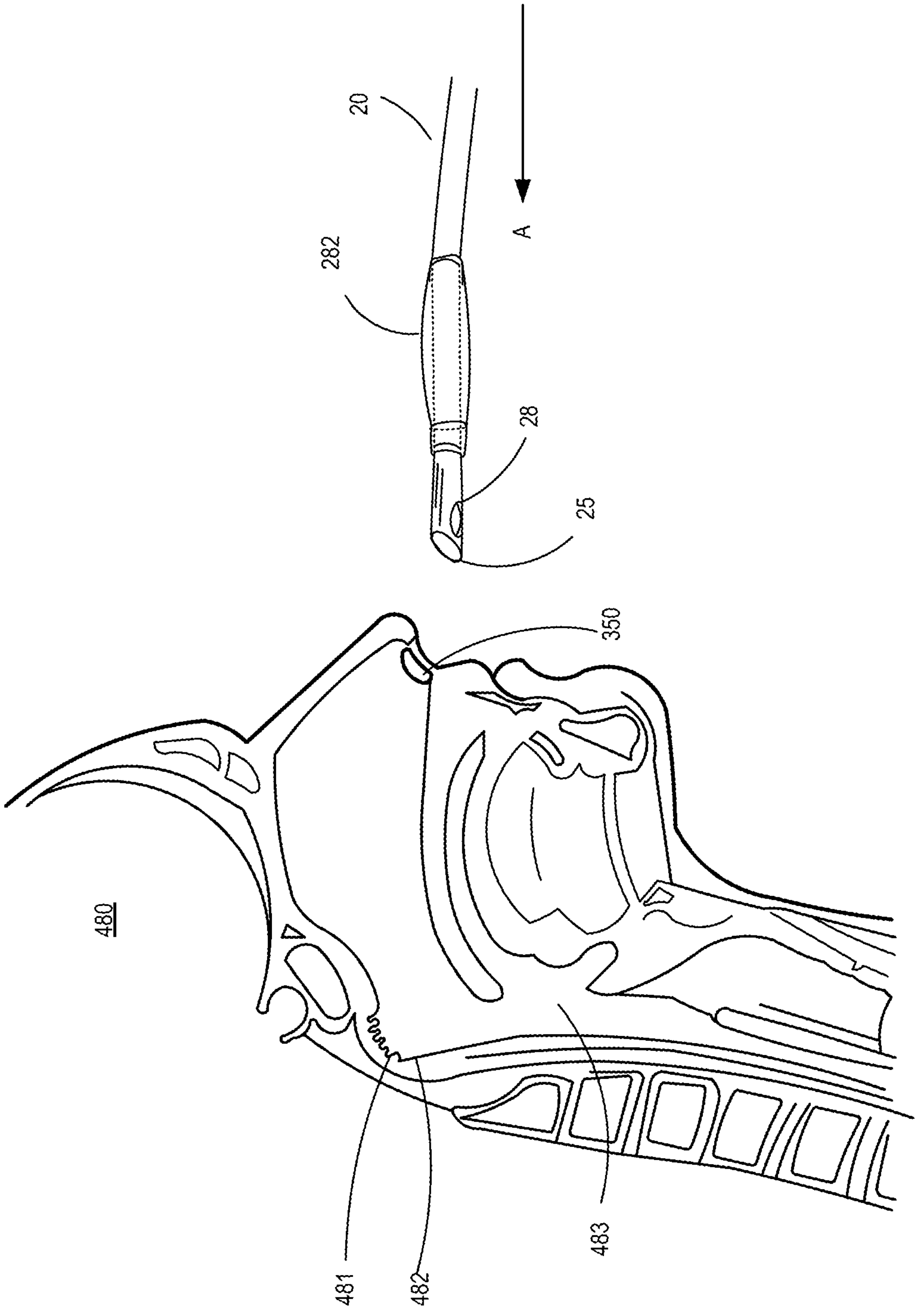
FIG. 1A (Prior Art)
FIGS. 1A-1B depicts an exemplary feeding tube of the prior art and its insertion into the nasopharynx of a patient.
Figure 1B:
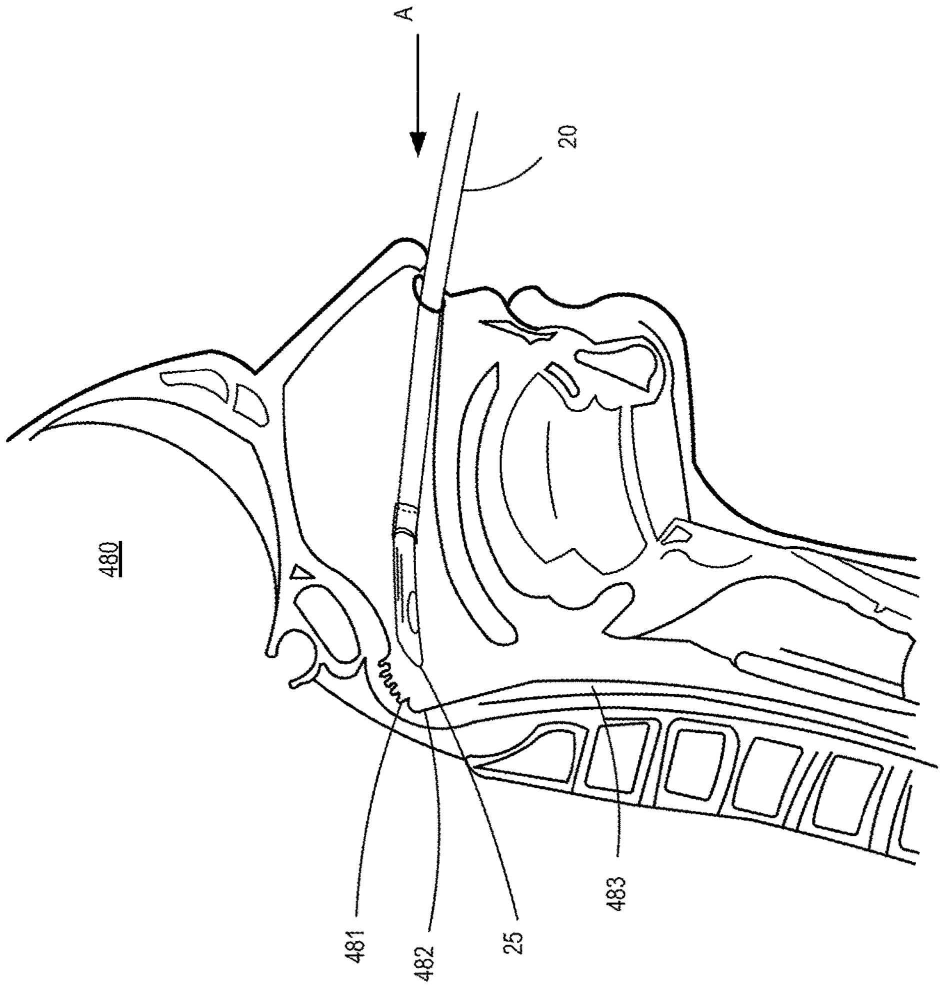
FIG. 1B (Prior Art)

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

The present invention is directed to methods of inserting a tube through the nasopharynx of a patient. The present invention is further directed to kits for inserting a tube through the nasopharynx of a patient. The present invention is even further directed to methods of making kits for inserting a tube through the nasopharynx of a patient.

I. Methods of Using Kits for Inserting a Tube Within the Nasopharynx of a Patient The present invention is directed methods of inserting a tube 20 through the nasopharynx 481 of a patient 480. In one exemplary embodiment, the method of inserting a tube 20 through the nasopharynx 481 of a patient 480 comprises: inserting the tube 20 through a naris 350 of the patient 480; and when a distal end 24 (with distal tip 25) of the tube 20 is proximate a rear surface 482 of the nasopharynx 481, pulling on and/or holding in place a thread-like member 70 attached to a tube portion 28 of the distal end 24 of the tube 20 so as to alter an initial direction A of the distal end 24 of the tube 20 and point the distal end 24 of the tube 20 towards a throat 483 of the patient 480. The method of inserting a tube 20 through the nasopharynx 481 of a patient 480 may further comprise a number of steps including, but not limited to, one or more of: advancing the distal end 24 of the tube 20 toward the throat area 483 of the patient 480 while pulling on the thread-like member 70; disengaging the thread-like member 70 from the tube 20; further advancing the distal end 24 of the tube 20 toward the throat area 483 of the patient 480 without the thread-like member 70; delivering one or more nutrients to the patient 480 through one or more openings or side holes 28 within the tube 20; and removing the tube 20 from the patient 480.

Figure 2A:
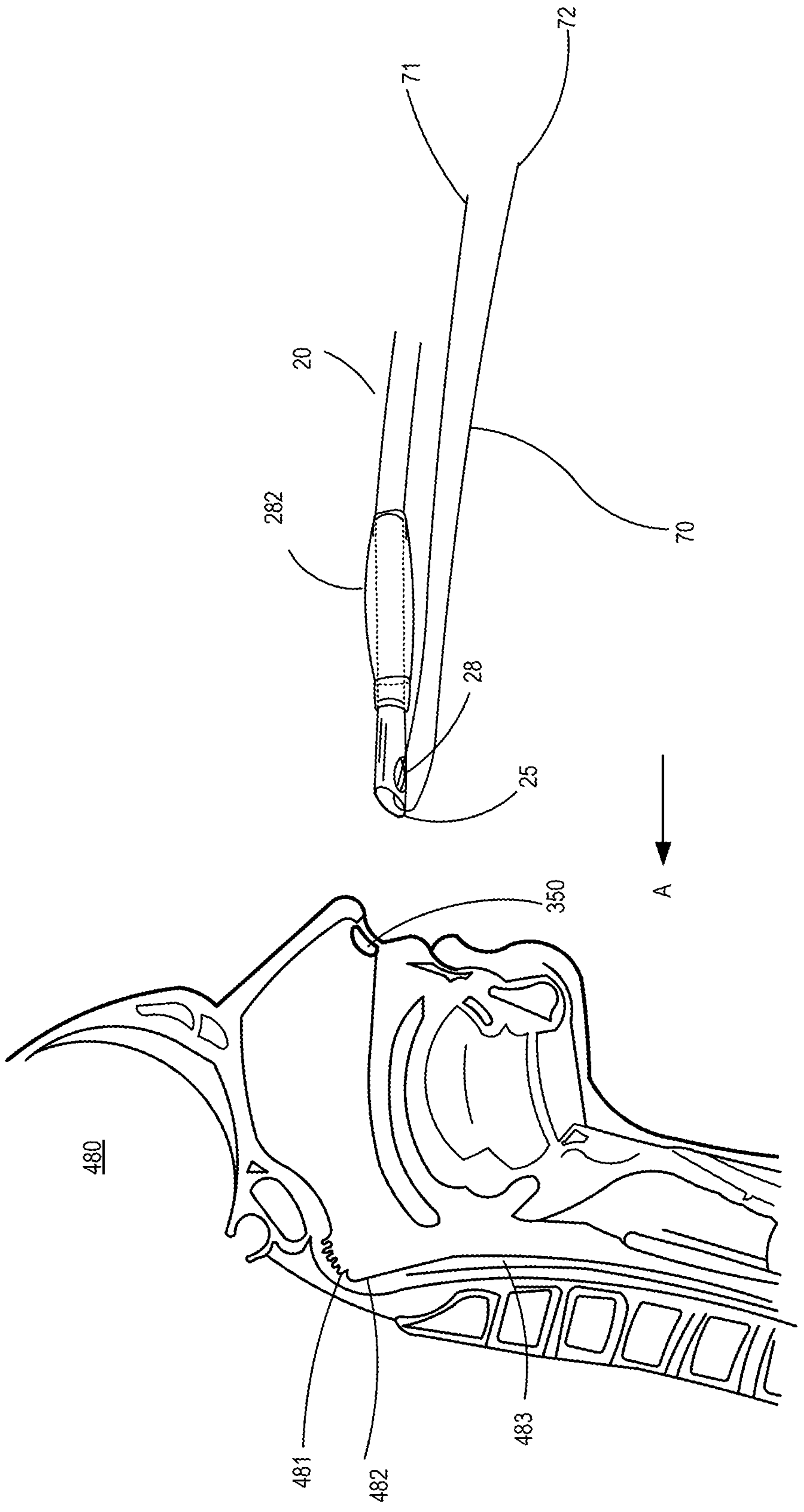
FIGS. 2A-2E depict an exemplary feeding tube kit/system and progressive steps showing its use in a method of inserting a tube through into the nasopharynx of a patient.

One exemplary method for inserting a tube 20 through the nasopharynx 481 of a patient 480 is shown in FIGS. 2A-2E. As shown in FIG. 2A, a method of inserting a tube 20 through the nasopharynx 481 of a patient 480 may comprise positioning a distal end 24 of a tube 20 and thread-like member 70 attached to a tube portion 28 of the distal end 24 of the tube 20 proximate a naris 350 of a patient 480.

Figure 2B:
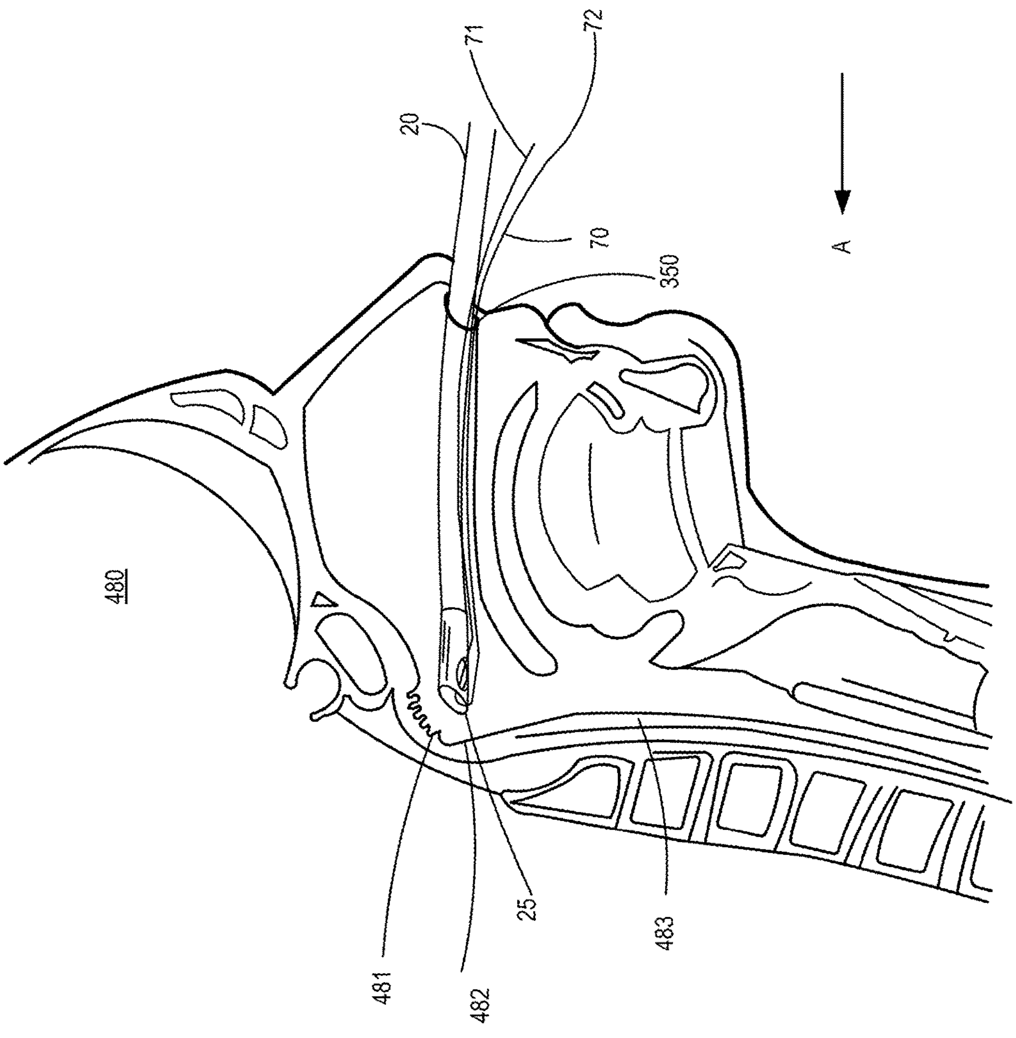

As shown in FIG. 2B, tube 20 and thread-like member 70 may be inserted through a naris 350 of the patient 480 so that a distal end 24 of the tube 20 is proximate a rear surface 482 of the nasopharynx 481. Desirably, distal end 24 of tube 20 is positioned a distance from rear surface 482, for example, such that distal tip 25 is less than about 15 millimeters (mm) from rear surface 482 of nasopharynx 481.

Figure 2C:
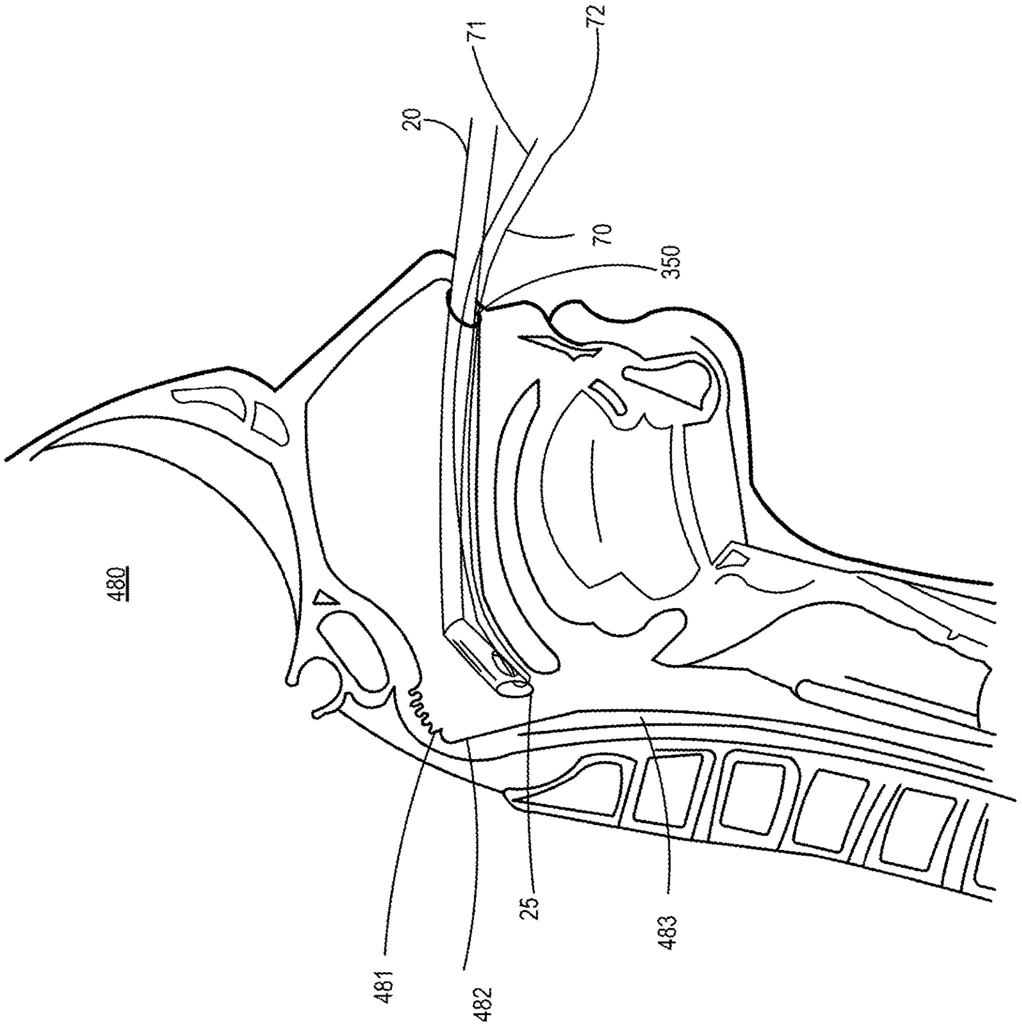

As shown in FIG. 2C, once distal end 24 of tube 20 is positioned a distance from rear surface 482, a user (not shown) can pull on and/or hold in place thread-like member 70 attached to a tube portion 28 of the distal end 24 of the tube 20 so as to alter an initial direction A (see FIGS. 2A-2B) of the distal end 24 of the tube 20 and point the distal end 24 of the tube 20 towards a throat 483 of the patient 480. For example, a user can advance the distal end 24 of the tube 20 towards throat 483 of patient 480 while holding in place the thread-like member 70. At some point, the user can continue to advance tube 20 after releasing tension (i.e., pull and/or hold in place tension) on thread-like member 70.

Figure 2D:
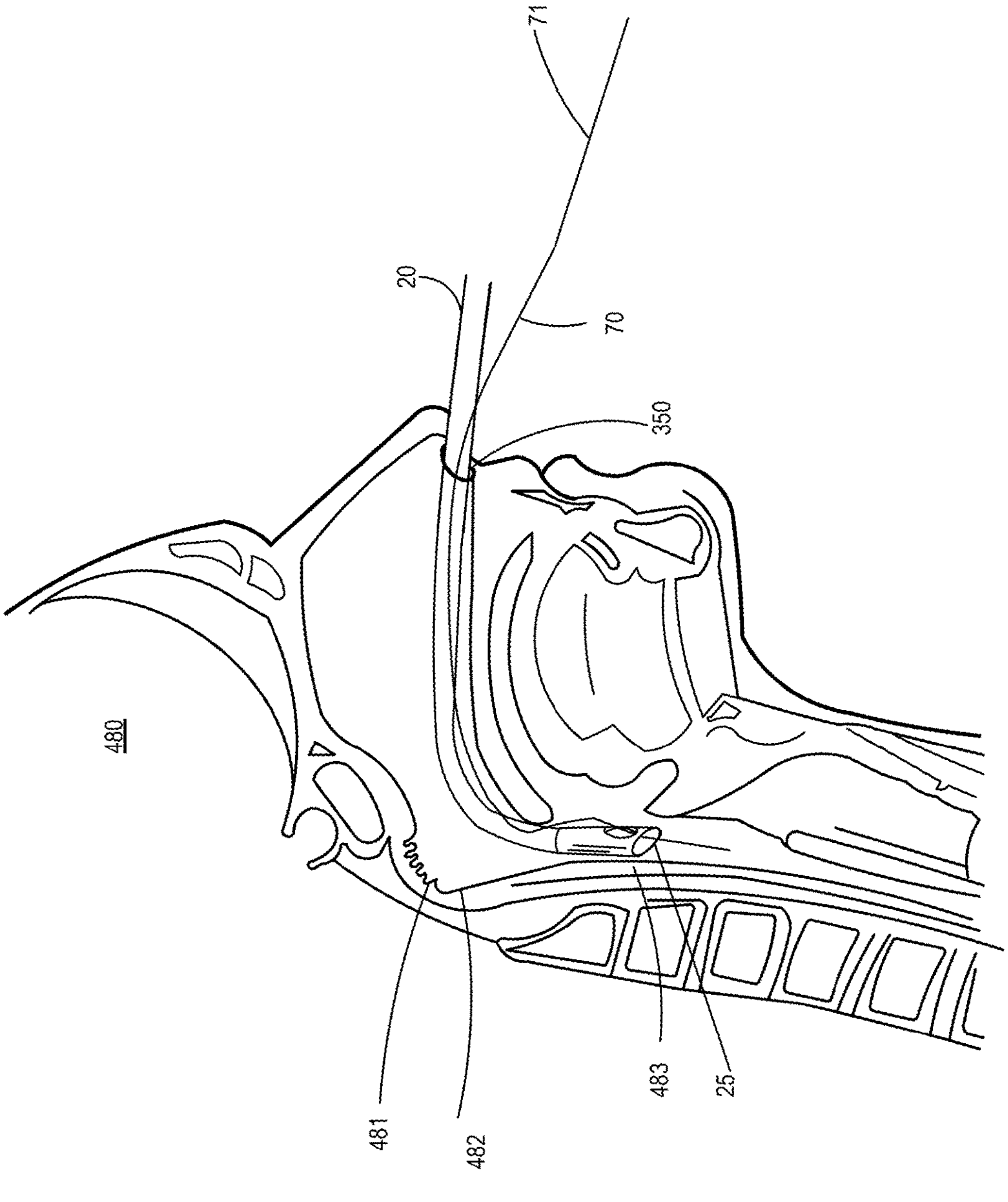
Figure 2E:
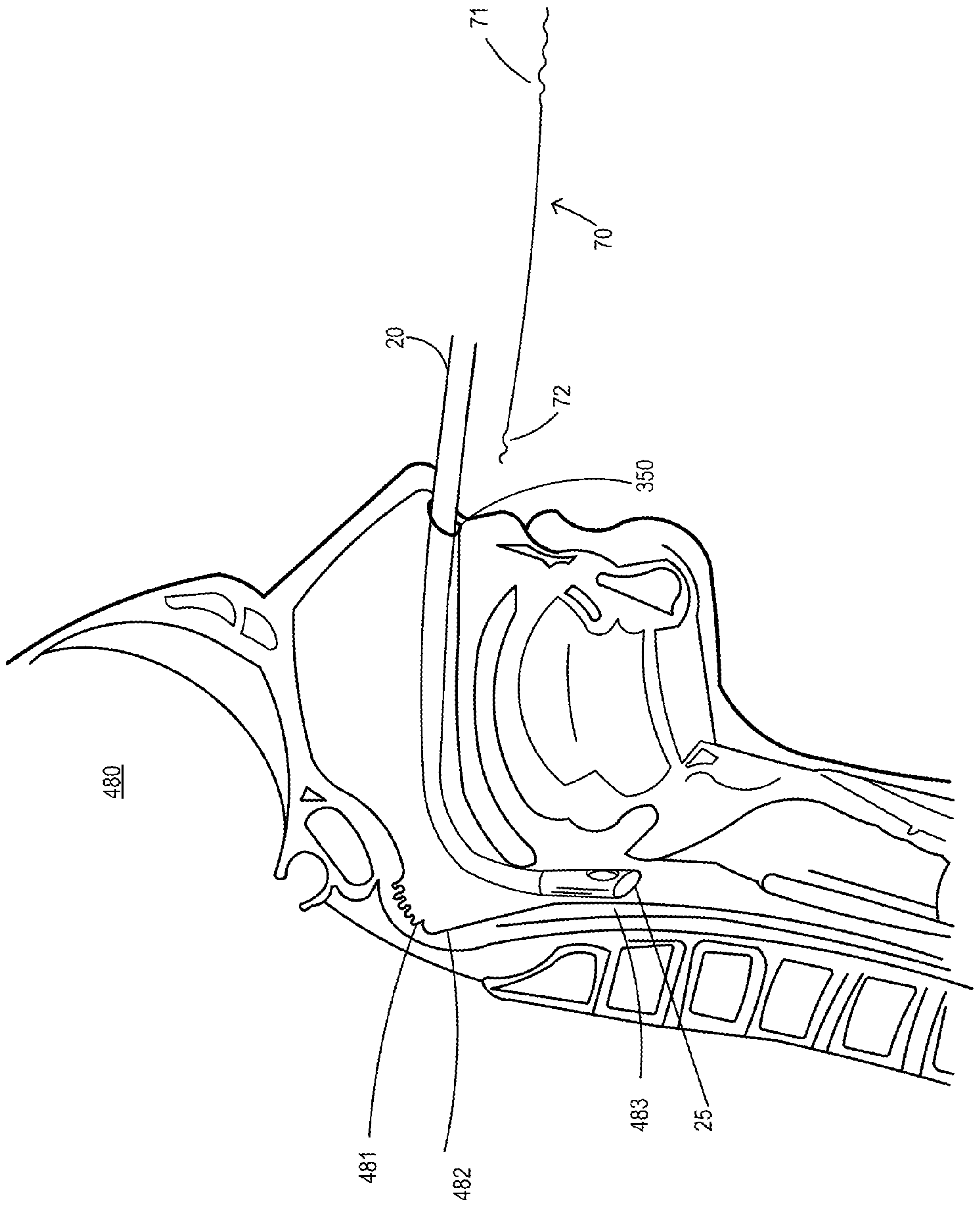

As shown in FIGS. 2D-2E, at some point, thread-like member 70 can be disengaged from tube 20. In some embodiments, thread-like member 70 can be disengaged from tube 20 by releasing one end 72 of thread-like member 70, and holding onto and/or pulling on an opposite end 71 of thread-like member 70 (FIG. 2D). At this time, tube 20 may be further advanced toward the throat area 483 of the patient 480 without the thread-like member 70. As shown in FIG. 2E, thread-like member 70 is removed from the patient 480.

Figure 12B:
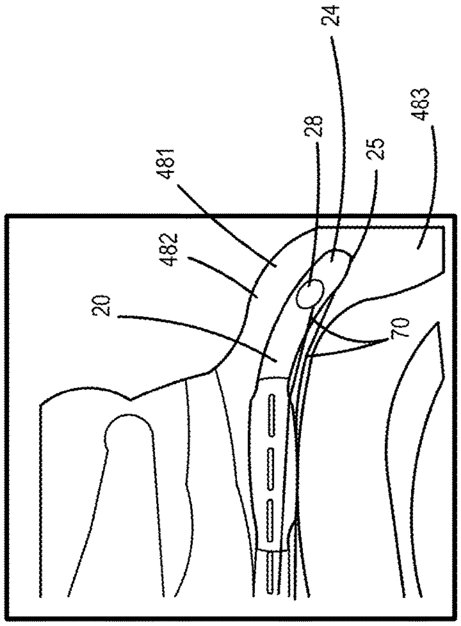
FIGS. 12A-12C depict another exemplary feeding tube kit/system and progressive steps showing its use in a method of inserting a tube through into the nasopharynx of a patient.
Figure 12C:
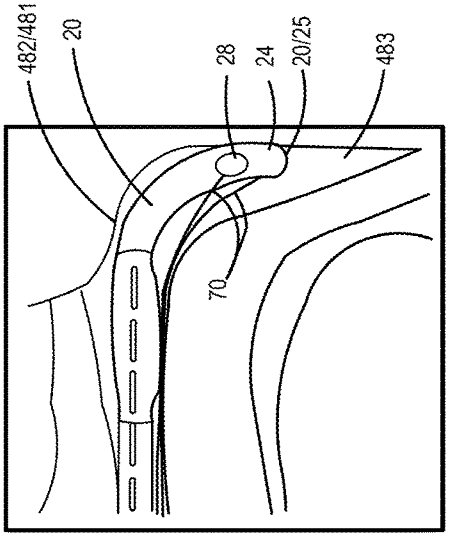
Figure 12A:
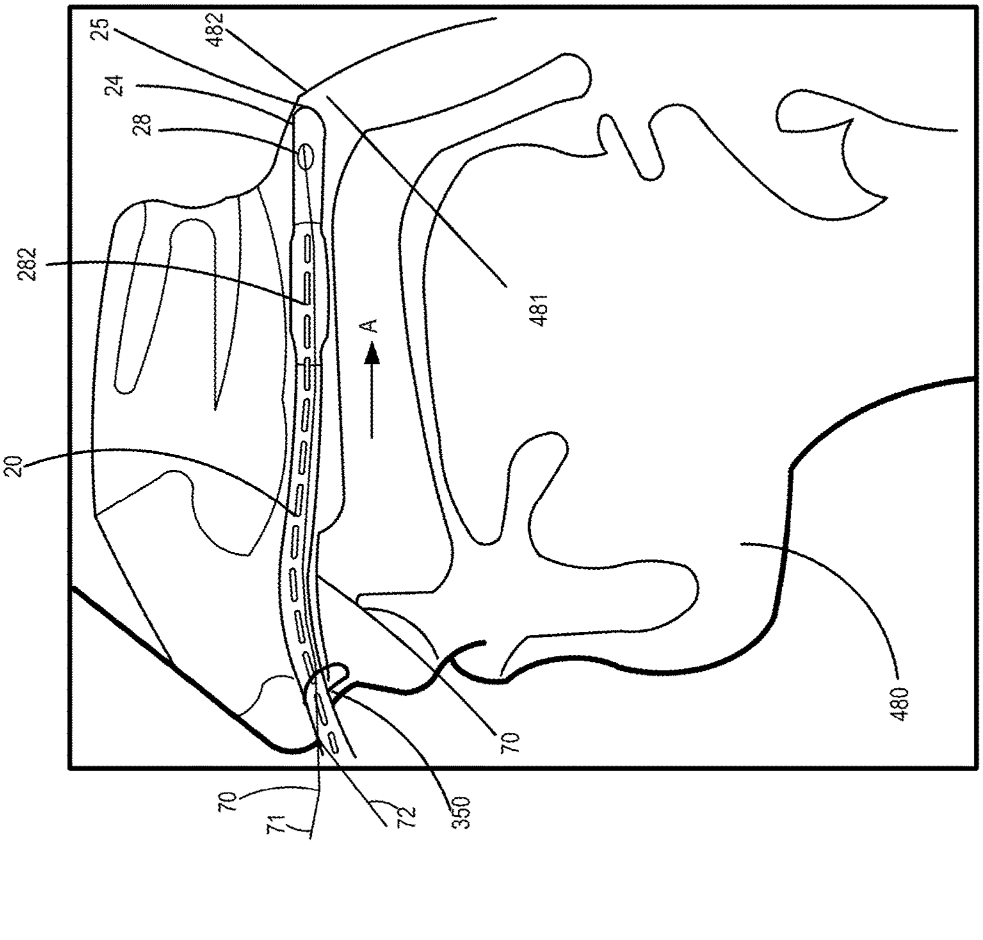

A similar exemplary method for inserting a tube 20 through the nasopharynx 481 of a patient 480 is shown in FIGS. 12A-12C. As shown in FIG. 12A, a method of inserting a tube 20 through the nasopharynx 481 of a patient 480 may comprise positioning a distal end 24 of a tube 20 and thread-like member 70 attached to a tube portion 28 of the distal end 24 of the tube 20 proximate a naris 350 of a patient 480, and then inserting tube 20 and thread-like member 70 through naris 350 of the patient 480 so that a distal end 24 of the tube 20 is proximate a rear surface 482 of the nasopharynx 481. Desirably, distal end 24 of tube 20 is positioned a distance from rear surface 482, for example, such that distal tip 25 is less than about 15 millimeters (mm) from rear surface 482 of nasopharynx 481.

As shown in FIGS. 12B-12C, once distal end 24 of tube 20 is positioned a distance from rear surface 482, a user (not shown) can pull on and/or hold in place thread-like member 70 attached to a tube portion 28 of the distal end 24 of the tube 20 so as to alter an initial direction A (see FIG. 12A) of the distal end 24 of the tube 20 and point the distal end 24 of the tube 20 towards a throat 483 of the patient 480 (see FIG. 12B). For example, a user can advance the distal end 24 of the tube 20 towards throat 483 of patient 480 while holding in place the thread-like member 70 (see FIG. 12C). At some point, the user can continue to advance tube 20 after releasing tension (i.e., pull and/or hold in place tension) on thread-like member 70.

In some desired embodiments, tube portion 28 of the distal end 24 of the tube 20 comprises one or more side holes 28 extending through a sidewall 201 of the tube 20; and the thread-like member 70 comprises thread or string 70 with a length of from about 20 to about 80 centimeters (cm), and a size so as to enable the thread or string 70 to extend through the one or more side holes 28.

In some desired embodiments, tube 20 comprises a feeding tube 20.

In some desired embodiments, tube 20 has an overall length $L_c$ ranging from about 100 to about 150 cm.

In some desired embodiments, the method of inserting a tube 20 through the nasopharynx 481 of a patient 480 comprises a method for intubating a patient 480 (see, FIG. 10) so as to introduce one or more nutrients into the duodenum of the patient 480, wherein the method comprises: tube 20 (i.e., shown as tube 20 of feeding tube apparatus 10 in FIGS. 5A-11) through the patient's stomach 380 until inflatable balloon component 282 of tube 20 passes through the pyloric sphincter 450; and inflating inflatable balloon component 282 of tube 20 so as to allow natural peristalsis of the patient 480 to further advance tube 20 comprising an inflated balloon component into the patient's duodenum 460.

The distal tip 25 of tube 20 is introduced into the naris 350 of the patient's nose and advanced using the techniques described above (see, for example, the technique shown in FIGS. 2A-2E). Distal tip 25 of tube 20 moves to the back portion of the patient's head and into the esophagus. As is common, the passageway of the esophagus affords ample guidance to distal tip 25 whereupon it enters the body portion of the stomach 380.

Figure 10:
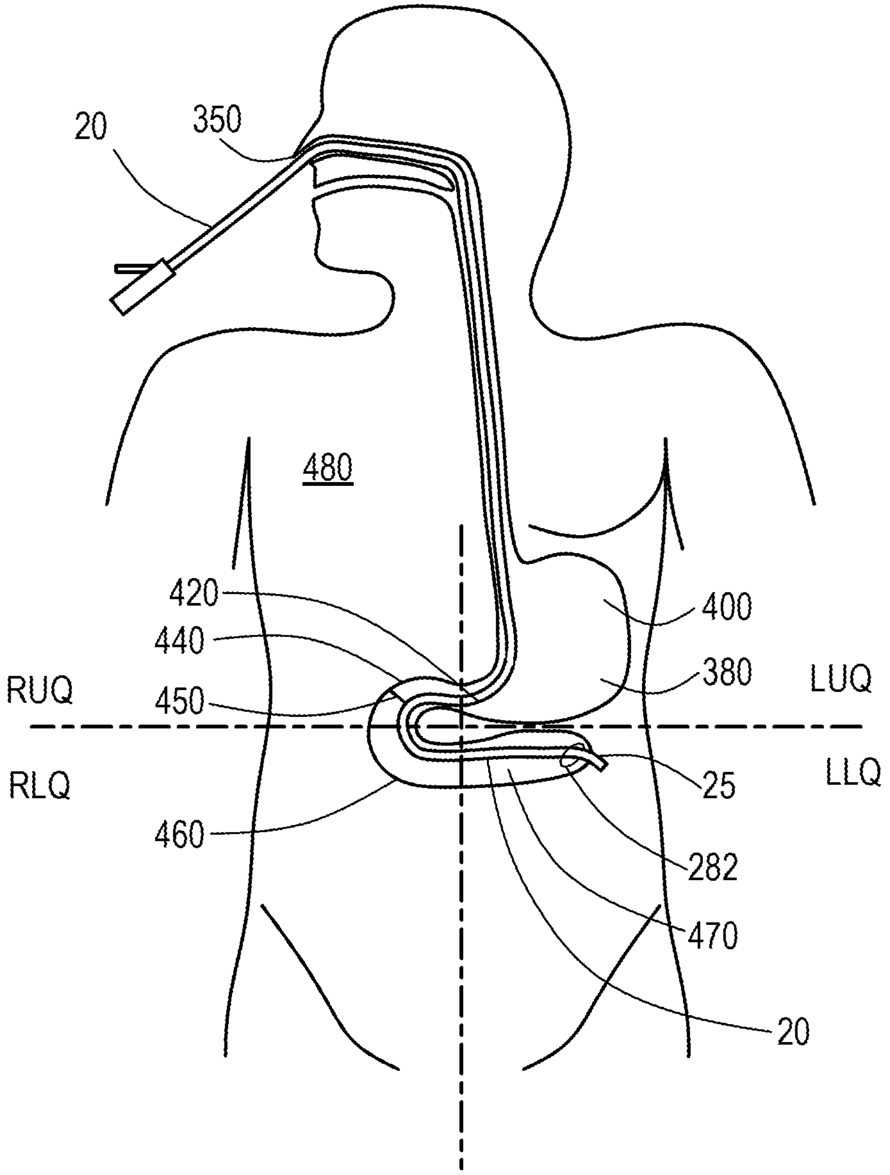
FIG. 10 depicts an illustration showing the path of an exemplary feeding tube apparatus suitable for use in the exemplary feeding tube kit/system shown in FIGS. 2A-2E within anatomical quadrants during passage through the stomach to the distal duodenum of the small intestine.

FIG. 10 is an illustration showing the path of tube 20 within anatomical quadrants of the small intestine abdomen. Tube 20 passes through the stomach 380 to the distal duodenum 470 to allow for feeding to occur in distal duodenum 470, and thereby prevent aspiration of fluids to stomach 380, and subsequently into the esophagus and lung in supine patients.

Stomach 380 has a generally J-shaped configuration extending with generally its largest transverse anatomical size at about the cardiac orifice, the entrance site to stomach 380, and then proceeding in the direction at which stomach 380 functions to advance bolus, the transverse dimension of stomach 380 narrows, and at an angular notch 420 which is generally at the border between the left upper quadrant (LUQ) and the right upper quadrant (RUQ). From annular notch 420, there commences a smaller transverse dimension at the pyloric part 440 typically residing in the right upper quadrant together with pyloric sphincter 450. Pyloric sphincter 450 is a muscular controlled closure, which will dilate as when a bolus comes into contact with the sphincter. Beyond the sphincter, a bolus passes into the duodenum portion 460 that extends to the right lower quadrant (RLQ), and then extends in a general horizontal direction into the left lower quadrant (LLQ) where the distal duodenum 470 of the small intestine is located.

II. Kit Components

Kits of the present invention may comprise one or more of the following possible kit components.

A. Tubes and Tube-Containing Articles

Figure 5A:
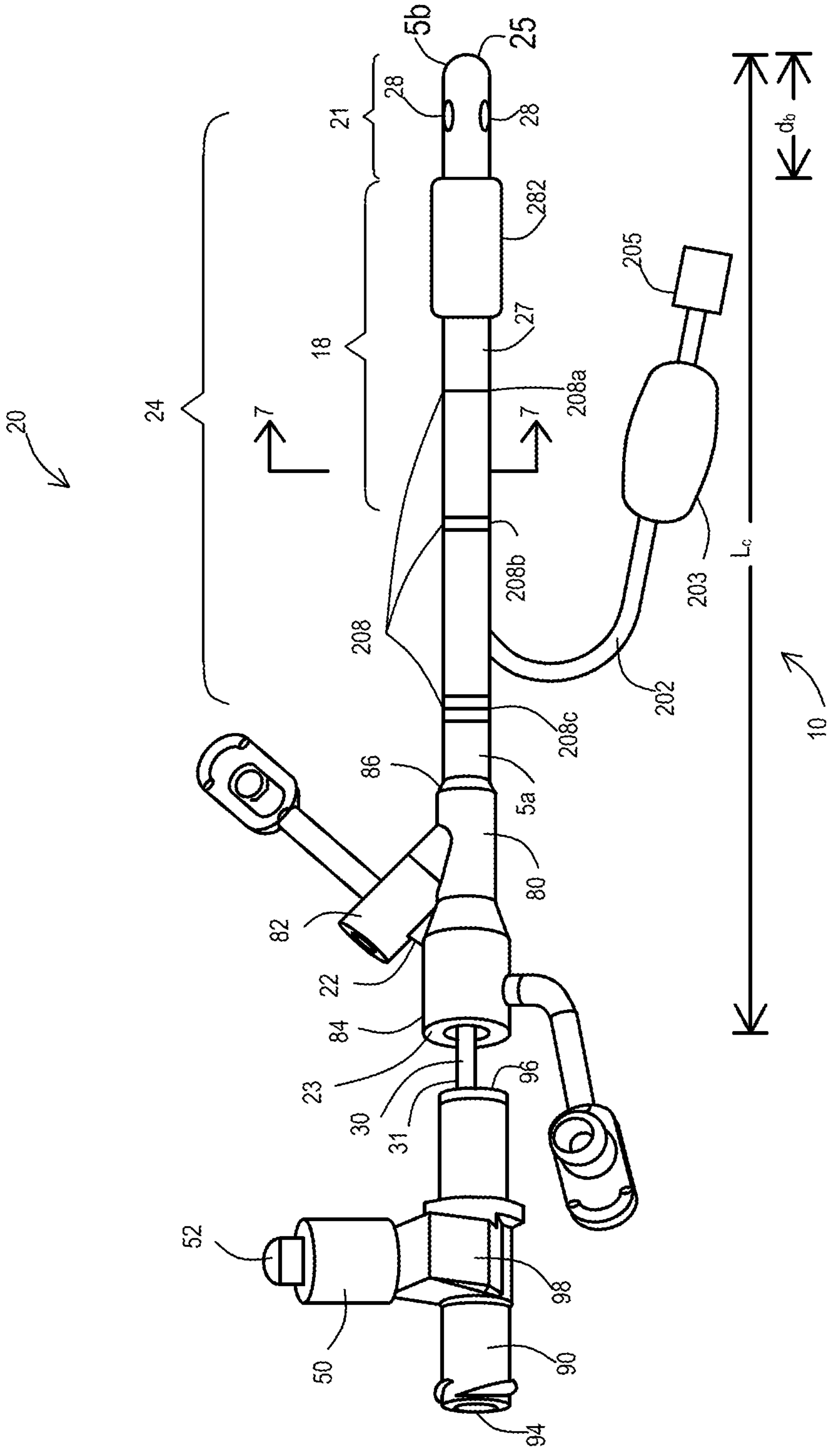
FIG. 5A depicts an exemplary feeding tube apparatus with an exemplary inflatable balloon component in a non-inflated state, the exemplary feeding tube apparatus being a suitable tube for use in the exemplary feeding tube kit/system shown in FIGS. 2A-2E.
Figure 5B:
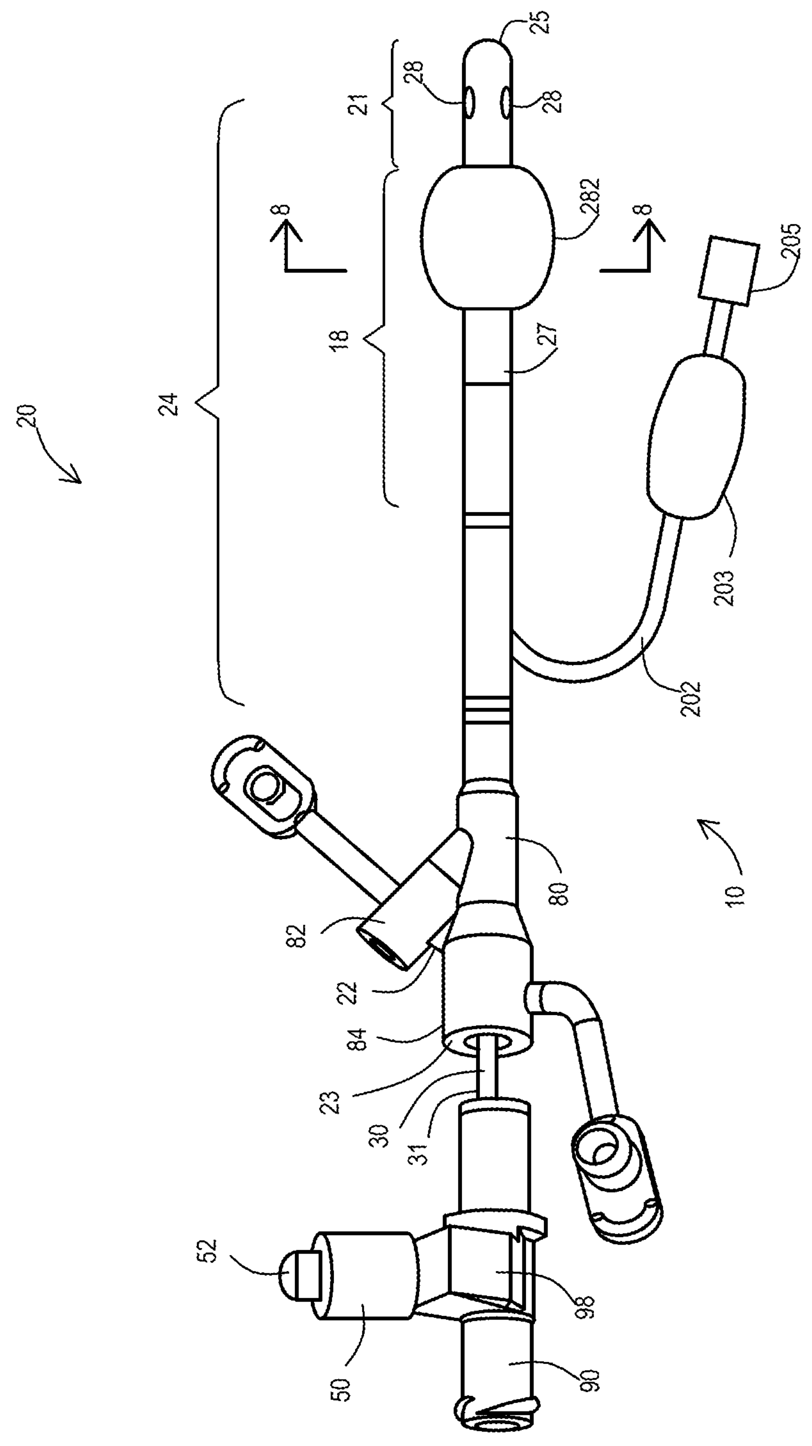
FIG. 5B depicts the exemplary feeding tube apparatus shown in FIG. 5A with the exemplary inflatable balloon component in an inflated state.

Kits of the present invention may comprise any of the herein-described tubes such as tube 20. In some embodiments, the tube 20 may be a component of a feeding tube apparatus such as exemplary feeding tube apparatus 10 shown in FIGS. 5A-5B. FIG. 5A depicts an exemplary tube 20 within feeding tube apparatus 10 with an exemplary inflatable balloon component 282 of tube 20 in a non-inflated state. FIG. 5B depicts exemplary feeding tube apparatus 10 shown in FIG. 5A with exemplary inflatable balloon component 282 of tube 20 in an inflated state.

As shown in FIGS. 5A-5B, feeding tube apparatus 10 may comprise one or more of the following components.

1. Tube

Figure 6A:
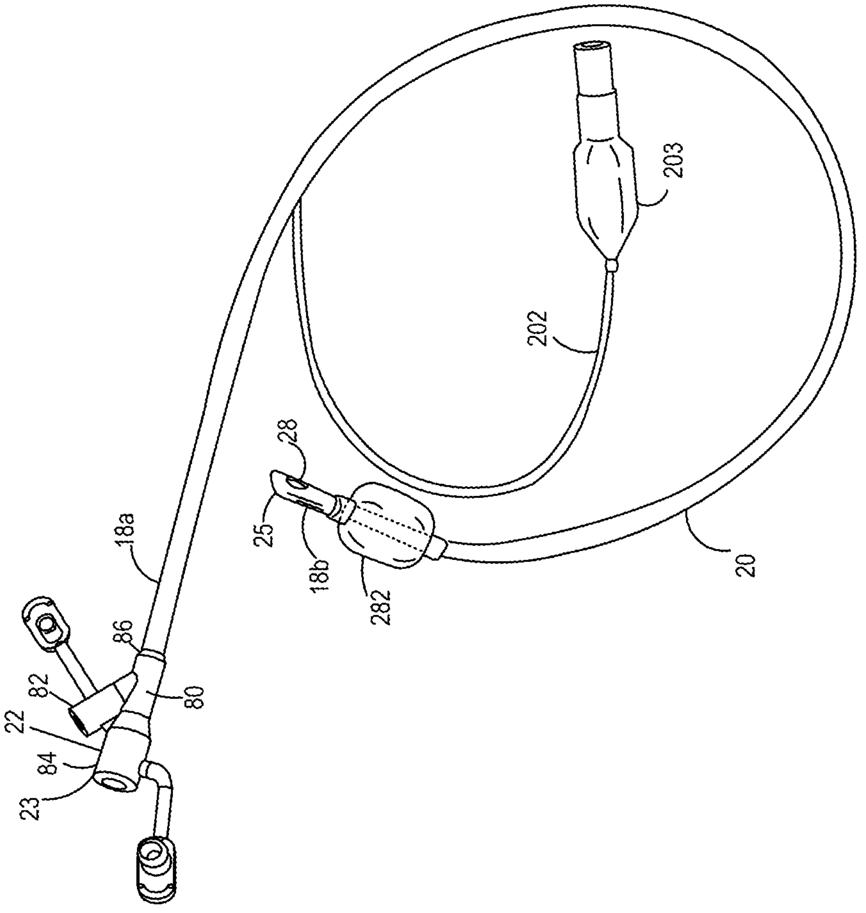
FIG. 6A depicts another exemplary feeding tube apparatus with an exemplary inflatable balloon component in an inflated state, the exemplary feeding tube apparatus being a suitable tube for use in the exemplary feeding tube kit/system shown in FIGS. 2A-2E.
Figure 6B:
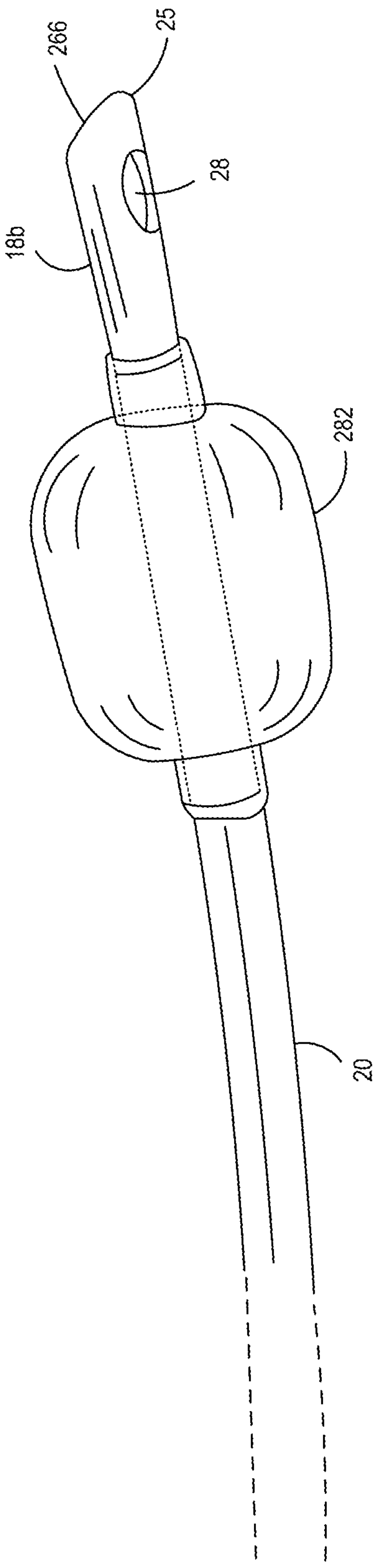
FIG. 6B depicts a close-up view of the distal end of the exemplary feeding tube apparatus shown in FIG. 6A.

Exemplary feeding tube apparatus 10 shown in FIGS. 5A-5B, comprise a tube 20. Tube 20 comprises a tube with a proximal end 22 and a distal end 24. Distal tip 25 of distal end 24 may be closed as shown in FIGS. 5A-5B, or may form an open lumen 266 as shown in FIGS. 6A-6B. Open lumen 266 allows for the delivery of food from distal tip 25 of tube 20. Alternatively, distal tip 25 of tube 20 is closed (as shown in FIG. 5A) and does not contain an open lumen. In this alternative embodiment, tube 20 may contain one or more side holes 28 for food/nutrient delivery to a patient 480.

As shown in FIGS. 6A-6B, even when distal tip 25 of distal end 24 forms an open lumen 266, tube 20 may comprise one or more side holes 28 for food/nutrient delivery to a patient and/or aspiration of fluid from the stomach (e.g., sampling by aspiration using a syringe to test acidity or alkalinity using pH paper) through the one or more side holes 28. As shown in FIGS. 6A-6B, exemplary tube 20 comprises an open lumen 266 at distal end 24, and a single side hole 28.

Distal tip 25 and the region 21 proximal to distal tip 25 may be formed of a softer material than the material that forms the rest of the tube 20. This allows distal tip 25 and region 21 proximal to distal tip 25 to be more flexible than if a stiffer material was used. However, in other embodiments, all portions of tube 20, including distal tip 25 and region 21, may be also formed from a single material (or combination of materials). Proximal end 22 of tube 20 also forms an opening 23 into which a removable stylet 30 may be placed when inserted into tube 20.

When distal end tip 25 comprises an open lumen 266, this allows for the use of a fiberscope, i.e. a flexible, small endoscope, which can be placed through open lumen 266 to verify the location of tube 20. The use of a fiberscope can eliminate the need for X-rays to be taken to verify the location of the tube 20.

Tube 20 may be formed of any suitable tubing. Typically, suitable tubing materials have a flex modulus ranging from about 500 psi to about 50,000 psi, preferably from 700 psi to 3,000 psi, most preferably about 1,500 psi. In one exemplary embodiment, the tubing is dual durometer tubing, with at least two levels of flexibility; where the flex modulus for a first, softer portion is lower than the flex modulus for a second, more rigid portion. In one embodiment, proximal end 22 comprises a first, relatively soft material, and distal end 24 is more rigid than proximal end 22. In another exemplary embodiment, the tubing is relatively soft at the tube's proximal end 22, at distal tip 25 and within region 21 proximate to distal tip 25, and is more stiff in the region 18 between proximal end 22 and region 21 proximate to distal tip 25. The soft material at proximal end 22, which will contact the patient's throat and nose, causes less irritation to the patient than a stiffer material. The soft portion of tube 20 typically has a flex modulus ranging from about 500 psi to 30,000 psi, preferably ranging from about 750 psi to 3,000 psi. The stiffer material in region 18 between proximal end 22 and region 21 proximal to distal tip 25 allows tube 20 to have greater pushability and maneuverability during insertion than if a softer material was included in region 18 of tube 20. The stiffer portion of tube 20 typically has a flex modulus ranging from about 1,500 psi to about 100,000 psi, preferably from about 10,000 psi to about 50,000 psi.

In one exemplary embodiment, tube 20 is constructed in whole or in part of a medical grade radio-opaque material. Suitable medical grade radio-opaque materials include, but are not limited to, polyurethane, polyvinyl chloride (PVC) or silicon tubing. In some embodiments, the tubing comprises a polyurethane for strength. Preferably, the polyurethane material does not soften or change significantly at body temperature. Examples of suitable polyurethanes include, but are not limited to, those available under the trade designations ESTANE® (Lubrizol Advanced Materials, Inc.), PEBAX® (Arkema France Corp.), PELLETHANE® (Dow Chemical Co.), and CARBOTHANE® (Lubrizol Advanced Materials, Inc.).

Figure 7:
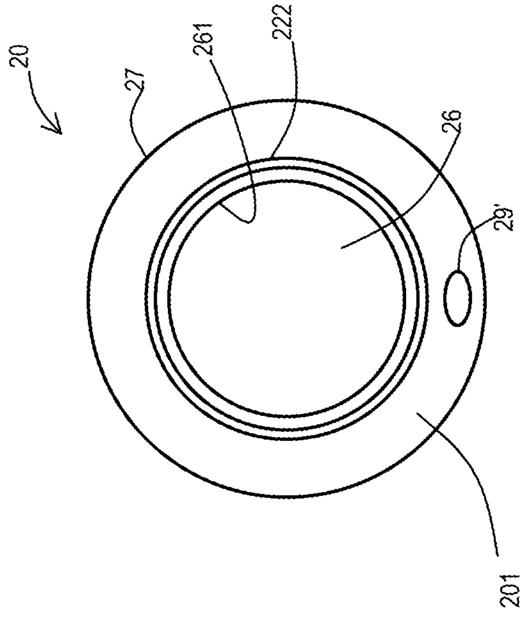
FIG. 7 depicts a cross-sectional view of the exemplary feeding tube apparatus shown in FIG. 5A along line 7-7 shown in FIG. 5A.
Figure 8:
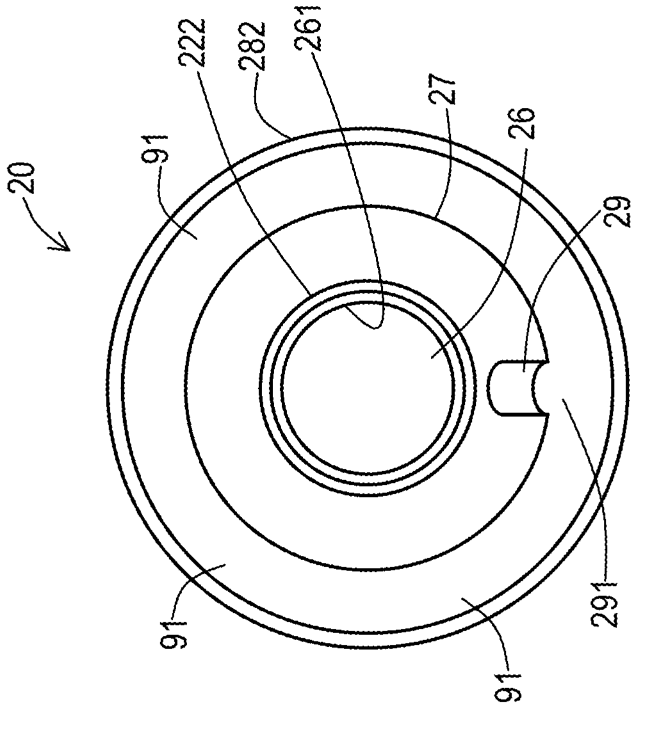
FIG. 8 depicts a cross-sectional view of the exemplary feeding tube apparatus shown in FIG. 5B along line 8-8 shown in FIG. 5B.
Figure 9:
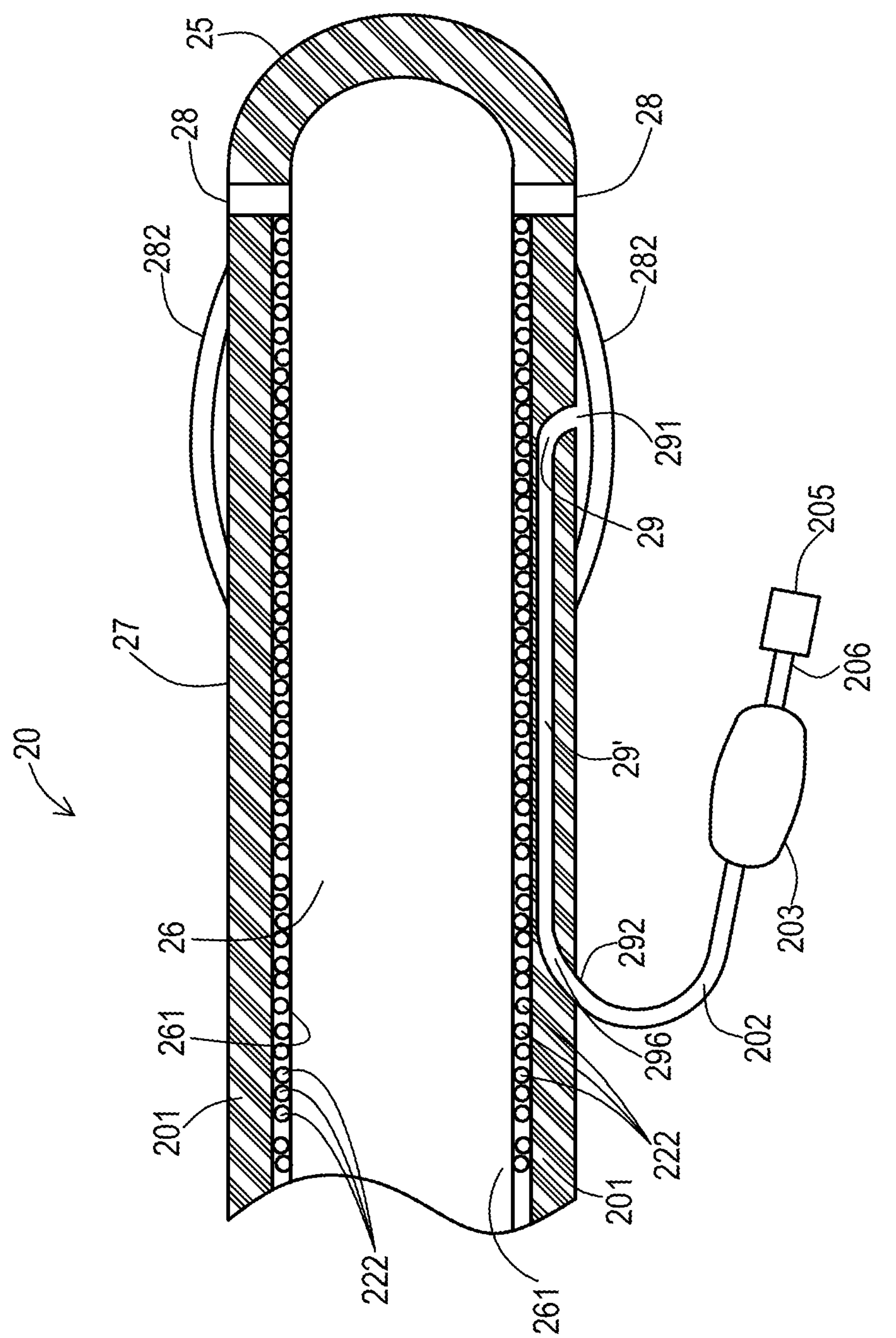
FIG. 9 depicts a cross-sectional view of a portion of the exemplary tube within the exemplary feeding tube apparatus shown in FIG. 5A from point 5*a* to point 5*b* shown in FIG. 5A.

In some embodiments, the walls of the tube 20 may contain a reinforcing material 222 e.g., as shown in FIGS. 7-9. In these embodiments, the walls 201 of tube 20 may contain, for example, an MRI compatible reinforcing material 222, such as a fiber, monofilament, or non-ferrous metal. This allows the tube 20 to have a thin wall, while maintaining the desired inner diameter. Reinforcing material 222 also provides kinking and/or crush-resistance to tube 20. Reinforcing material 222 also allows tube 20 to be especially resilient to perforation, thereby facilitating the use of a plunger (not shown) to purge a clogged tube 20 without the risk of perforating or damaging the feeding tube 10, even when the tube 10 is conforming to a tortuous path in the patient's body.

When present, reinforcing material 222 may be present as a coil reinforcing material 222 (e.g., a metal coil 222) as shown in FIGS. 7-9. Coil reinforcing material 222 may extend a complete length $L_c$ of tube 20, or less than the complete length $L_c$. For example, in some embodiments, coil reinforcing material 222 extends the complete length $L_c$ of tube 20 except for about one centimeter on either end of tube 20. See, for example, FIG. 6A, wherein a metal coil reinforcing material (i.e., embedded within wall 201 or along an inner surface 261 of wall 201) extends from point 18*a* to point 18*b* along tube 20. In other embodiments, coil reinforcing material 222 extends from about point 5*a* to one or more side holes 28 of tube 20. In other embodiments, coil reinforcing material 222 extends from about point 5*a* to distal tip 25 of tube 20.

In some embodiments, coil reinforcing material 222 is embedded within wall 201 of tube 20 as shown in FIGS. 7-9. However, in other embodiments (not shown), coil reinforcing material 222 extends along inner surface 261 of wall 201 of tube 20 so as to form an inner surface (i.e., that comes into contact with removable stylet 30 when inserted). When coil reinforcing material 222 extends forms an inner surface of tube 20, the contact surface of coil reinforcing material 222 (i.e., the surface that comes into contact with removable stylet 30) may further comprise a coating (not shown) that minimizes friction between tube 20 and removable stylet 30.

Any standard diameter and length of tubing material may be used to form the tube 20. Standard tube sizes are referred to as "French" sizes, e.g. size F4 refers to a tube with a 0.053 inch outer diameter, F5 refers to a tube with a 0.066 inch outer diameter, F6 refers to a tube with a 0.079 inch outer diameter, F7 refers to a tube with a 0.092 inch outer diameter, F8 refers to a tube with a 0.104 inch outer diameter, F10 refers to a tube with a 0.131 inch outer diameter, F11 refers to a tube with a 0.143 inch outer diameter, and F12 refers to a tube with a 0.156 inch outer diameter. In one exemplary embodiment, the tubing is a single lumen 2603-80AE PELLETHANE® F11 or F12 tube. The F11 tube has an outer diameter of 0.143 inches and an inner diameter of 0.111 inches; and the F12 tube has an outer diameter of 0.156 inches and an inner diameter of 0.116 inches. However other size tubing is suitable as well. In place of single lumen tubing, double lumen tubing or alternative styles may be used. The inner diameter of the tubing (i.e. the diameter of the lumen) should be sufficiently large to allow the fluids and nutrients to pass through tube 20 without clogging tube 20. Typically, the inner diameter of the tubing (i.e. the diameter of the lumen) is sufficiently large to allow particles with a diameter of up to 0.110 inches to pass through the tubing.

Typical lengths for tube 20 range from about 100 cm to about 150 cm. More typically, tube 20 is at least 125 cm long. In one exemplary embodiment, tube 20 is 127 cm long. This allows for nutrients to be delivered deep into the bowel and thereby prevent reflux. Tubes/tubes 20 that are at least 100 cm long prevent the patient from inadvertently removing the feeding tube 20 after placement in the stomach such as through standard movements.

In addition to openings 23 and 266 at proximal and distal ends 22 and 24 of tube 20, tube 20 may further comprise one or more side holes 28 along and within wall 201 of tube 20. In some embodiments, side holes 28 are located as close to distal tip 25 as possible without compromising the strength of the tubing. In one embodiment, side holes 28 are located in region 18 between the proximal end 22 and inflatable balloon component 282. In another embodiment, side holes 28 are located within region 21 proximate to distal tip 25 of tube 20.

Side holes 28 ensure that, even if feeding tube 10 is lodged against a wall in a patient's body, aspirating tube 20 will not create a suction situation and potentially damage internal tissues or walls.

In one exemplary embodiment, tube 20 comprises a single side hole 28 as shown in FIGS. 6A-6B. In another exemplary embodiment, tube 20 comprises two side holes 28 as shown in FIGS. 5A-5B. Side holes 28 are typically oval or circular in shape and typically have dimensions ranging from about 0.060 inches to about 0.300 inches, more typically about 0.120 inches.

2. Inflatable Balloon Component

Exemplary tube 20 may further comprise an inflatable balloon component, such as inflatable balloon component 282 shown in FIGS. 5A-5B. Inflatable balloon component 282 comprises an inflatable material that may be pliable or non-pliable. Suitable materials for forming inflatable balloon component 282 include, but are not limited to, polyvinyl chloride (PVC), silicon, latex, medical grade rubber, nitrile, and ChronoPrene™ material.

Inflatable balloon component 282 is positioned along an outer surface 27 of tube 20, typically proximate distal end tip 25. Inflatable balloon component 282 may be attached to outer surface 27 of tube 20 via any known method of attaching one material to another. Suitable ways to attach inflatable balloon component 282 to outer surface 27 of tube 20 include, but are not limited to, adhesives, heat-bonding, ultrasonic welding, etc. Suitable adhesives include, but are not limited to, Permabond® 4C20 (an ethyl cyanoacrylate-containing composition), and Permabond® 4C10 (an ethyl cyanoacrylate-containing composition).

Figure 11:
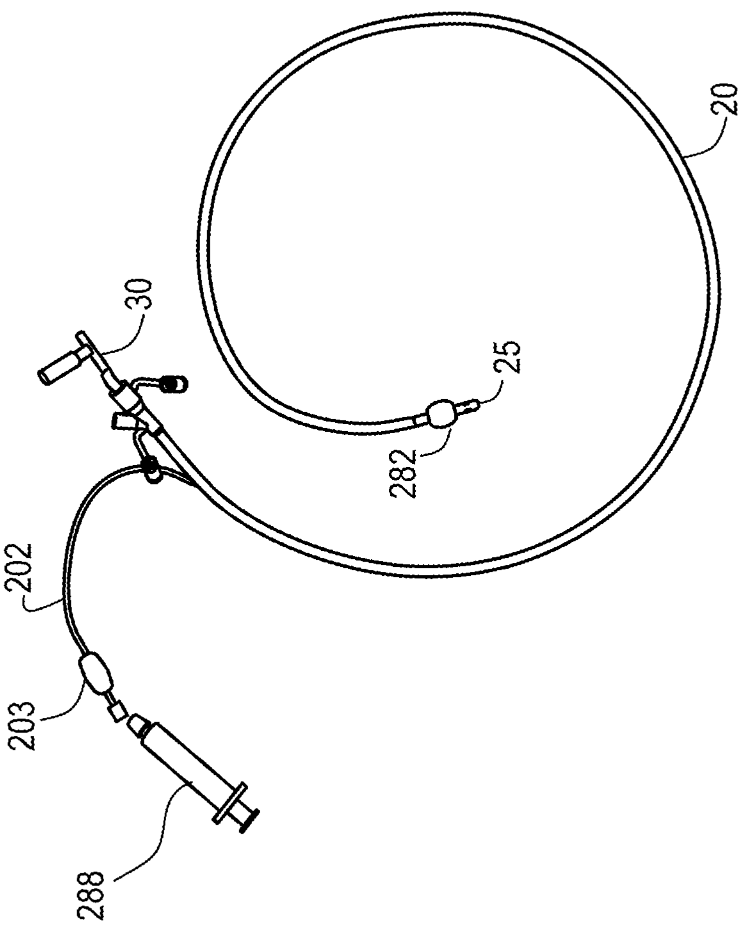
FIG. 11 provides another exemplary feeding tube suitable for use in the exemplary feeding tube kit/system shown in FIGS. 2A-2E.

Inflatable balloon component 282 may be inflated via at least one inflation tube 202 and an inflating device (e.g., a syringe 288 as shown in FIG. 11) as shown in FIG. 5A. Each inflation tube 202 may connect with an inflation channel 29' extending along a length $L_c$ of tube 20 and within a sidewall 201 of tube 20. Each inflating channel 29' comprising an inflating channel inlet opening 292 proximate tube proximal end 22 and an inflating channel outlet opening 291 along an outer surface 27 of tube 20 positioned underneath inflatable balloon component 282. FIG. 7 depicts a cross-sectional view of exemplary tube 20 shown in FIG. 5A along line 7-7 shown in FIG. 5A so as to illustrate an exemplary inflation channel 29'.

FIG. 8 depicts a cross-sectional view of exemplary tube 20 shown in FIG. 5B along line 8-8 shown in FIG. 5B. As shown in FIG. 8, inflating channel outlet opening 291 is positioned along outer surface 27 of tube 20 underneath inflatable balloon component 282.

FIG. 9 depicts a cross-sectional view of a portion of exemplary tube 20 within exemplary feeding tube apparatus 10 shown in FIG. 5A from point 5*a* to point 5*b* shown in FIG. 5A. As shown in FIG. 9, inflating channel 29' comprising an inflating channel inlet opening 292 proximate tube proximal end 22 and an inflating channel outlet opening 291 along an outer surface 27 of tube 20 positioned underneath inflatable balloon component 282.

Each inflation tube 202 may be attached to tube 20 via any known method of attaching one material to another. Suitable ways to attach inflatable balloon component 282 to outer surface 27 of tube 20 include, but are not limited to, adhesives, heat-bonding, ultrasonic welding, etc. Suitable adhesives include, but are not limited to, Permabond® 4C20 (an ethyl cyanoacrylate), and Permabond® 4C10 (an ethyl cyanoacrylate). Further, although not shown in FIG. 9, a portion of inflation tube 202 may extend into and be attached to an inner surface 296 of inflating channel 29' proximate inflating channel inlet opening 292.

3. Removable Stylet

Exemplary feeding tube apparatus 10 shown in FIGS. 5A-5B may further comprise a removable stylet, such as removable stylet 30. Removable stylet 30 comprises a proximal end 31 and a stylet distal end (not shown, but positioned within tube 20 shown in FIG. 5A), with distal end terminating in a stylet distal tip (not shown, but positioned within tube 20 shown in FIG. 5A). As shown in FIGS. 5A-5B, removable stylet 30 further comprises stylet hub 90, a stylet hub port 98 for attachment of a signal generator 50, and a signal indicator (e.g., LED light) 52. The proximal end 84 of feeding tube hub 80 attaches to the distal end 96 of stylet hub 90. Stylet hub 90 contains an opening at each end (i.e., proximal end 94 and distal end 96) and is hollow throughout the length of stylet hub 90. Port 98 preferably contains a socket with which an LED plug can connect and thereby provide a visual signal when an external magnet (not shown) is at an appropriate distance from magnetic material (s) (not shown).

Suitable removable stylets and removable stylet components/features are disclosed in U.S. Pat. No. 9,713,578 (Gabriel), the contents of which is herein incorporated by reference in its entirety.

4. Optional Components

Suitable optional components/features for feeding tubes are disclosed in U.S. Pat. No. 9,713,578 (Gabriel), the contents of which is herein incorporated by reference in its entirety.

B. Thread or Thread-Like Component

Kits of the present invention also include a thread-like member 70 that is attachable to a tube portion 28 of a distal end 24 of any of the herein-described (as well as other) tubes 20 and can be tensioned so as to alter an initial direction (e.g., direction A shown in FIGS. 2A-2B) of the distal end 24 of the tube 20 and point the distal end 24 of the tube 20 towards a throat 483 of a patient 480.

In some embodiments, the thread-like member 70 comprises a thread or a string 70 with a length of from about 20 to about 80 centimeters (cm), and a size so as to enable the thread or string 70 to extend through one or more side holes 28 along distal end 24 of tube 20. In some desired embodiments, thread-like member 70 comprises a silk thread such as Ethicon 2-0 silk suture from Ethicon U.S., LLC, (Somerville, N.J.) (or any other commercially available suture available from Ethicon U.S., LLC under the PERMA-HAND® brand).

C. Optional Kit Components

The kits of the present invention comprise one or more of the tubes described herein (e.g., a feeding tube apparatus 10 or tube 20 alone as described above), and one or more thread-like components 70 as described above. The kits may further comprise one or more additional components that assist the medical practitioner in use of the herein-disclosed kits.

Figure 3:
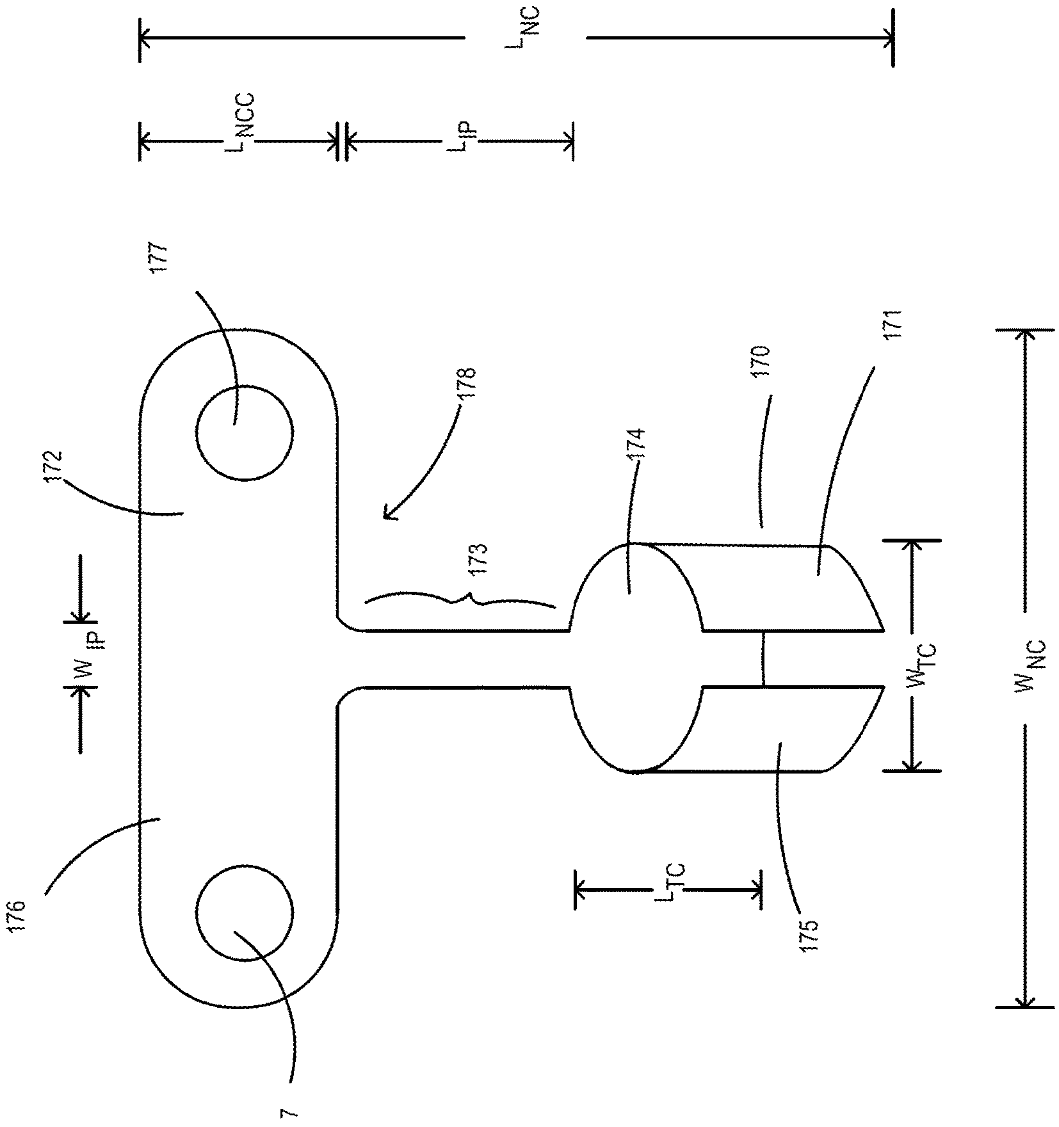
FIG. 3 depicts an exemplary tube-fastening member that may be used to fasten the feeding tube shown in FIGS. 2A-2E onto the nose of the patient.
Figure 4:
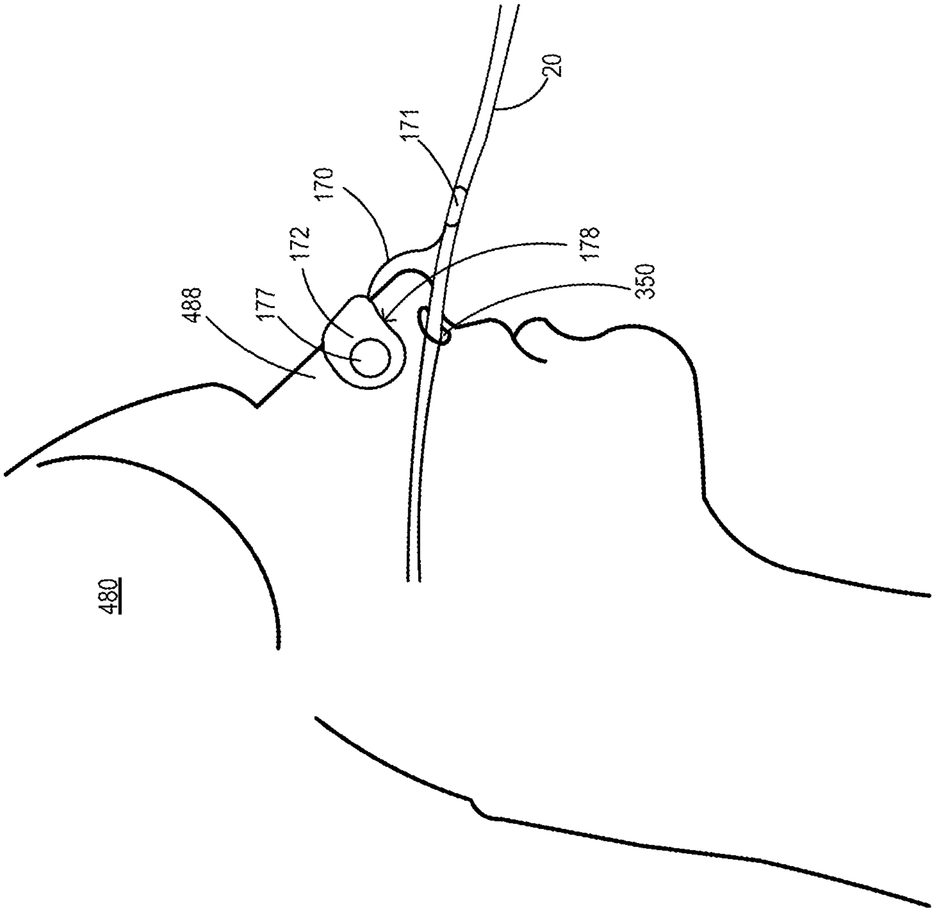
FIG. 4 depicts the exemplary tube-fastening member shown in FIG. 3 attached to the nose of a patient.

In some embodiments, the kit comprises a tube-fastening member such as exemplary tube-fastening member 170 shown in FIGS. 3-4. As shown in FIG. 3, exemplary tube-fastening member 170 comprises a tube-connector component 171 and a nose-connector component 172 separated from and connected to one another by an intermediate portion 173. Tube-connector component 171 comprises an inner tube surface 174 and an outer tube surface 175. Nose-connector component 172 comprises an upper nose-connector surface 176 and a lower nose-connector surface 178 opposite upper nose-connector surface 176. Nose-connector component 172 may further comprise one or more openings 177 extending through a thickness of Nose-connector component 172.

Exemplary tube-fastening member 170 may have any desired dimensions. Typically, exemplary tube-fastening member 170 has an overall length $L_{NC}$ of from about 40 mm to about 80 mm, and an overall width $W_{NC}$ of from about 30 mm to about 70 mm; tube-connector component 171 has a length $L_{TC}$ of from about 10 mm to about 30 mm, and an overall width $W_{TC}$ of from about 6.0 mm to about 16 mm; nose-connector component 172 has an overall length $L_{NCC}$ of from about 10 mm to about 20 mm, an overall width $W_{NCC}$ of from about 30 mm to about 70 mm, and a thickness of from about 0.8 mm to about 1.4 mm; intermediate portion 173 has an overall length $L_{IP}$ of from about 15 mm to about 40 mm, and an overall width $W_{IP}$ of from about 2.0 mm to about 10 mm; and each of one or more openings 177, when present, has a diameter of about 6.0 mm. In one desired embodiment, exemplary tube-fastening member 170 has an overall length $L_{NC}$ of about 58 mm, and an overall width $W_{NC}$ of about 50 mm; tube-connector component 171 has a length $L_{TC}$ of from about 20 mm, and an overall width $W_{TC}$ of about 10 mm; nose-connector component 172 has an overall length $L_{NCC}$ of about 12 mm, an overall width $W_{NCC}$ of about 50 mm, and a thickness of 1.0 mm; and intermediate portion 173 has an overall length $L_{IP}$ of about 25 mm, and an overall width $W_{IP}$ of about 3.0 mm.

As shown in FIG. 4, exemplary tube-fastening member 170 may be used to fasten a tube 20 (e.g., a feeding tube 20) that has been positioned within the nose of a patient (e.g., using the kit/system and method shown in FIGS. 2A-2E). As shown in FIG. 4, tube-connector component 171 may at least partially surround tube 20 so that an outer surface 27 of tube 20 contacts inner tube surface 174 and lower nose-connector surface 178 of nose-connector component 172 is attached to the nose 488 of patient 480 via, for example, an adhesive.

Other suitable additional kit components may include, but are not limited to, a syringe, preferably a 60 CC syringe; one or more towels; one or more cups; disposable gloves; Xylocaine gel (e.g. 2% Xylocaine gel); tape; gauze; and/or pH paper. Kits may further comprise a plunger or obturator that can clear clogs in tube 20 to eliminate the need to remove tube 20 and replace with another one. Kits may also comprise a spring wire guide that can be inserted into tube 20 after removable stylet 30 is removed.

The methods and kits for inserting a tube through the nasopharynx of a patient are further described in the following embodiments.

Other Embodiments

Methods for Inserting a Tube Through the Nasopharynx of a Patient

1. A method of inserting a tube 20 through a nasopharynx 481 of a patient 480, said method comprising: inserting the tube 20 through a naris 350 of the patient 480; and when a distal end 24 of the tube 20 is proximate a rear surface 482 of the nasopharynx 481, pulling on and/or holding in place a thread-like member 70 attached to a tube portion 28 of the distal end 24 of the tube 20 so as to alter an initial direction A of the distal end 24 of the tube 20 and point the distal end 24 of the tube 20 towards a throat 483 of the patient 480.

2. The method of embodiment 1, further comprising: advancing the distal end 24 of the tube 20 toward the throat area 483 of the patient 480 while pulling on and/or holding in place the thread-like member 70.

3. The method of embodiment 1 or 2, further comprising: advancing the distal end 24 of the tube 20 toward the throat area 483 of the patient 480 while holding in place the thread-like member 70.

4. The method of any one of embodiments 1 to 3, further comprising: disengaging the thread-like member 70 from the tube 20; and further advancing the distal end 24 of the tube 20 toward the throat area 483 of the patient 480 without the thread-like member 70.

5. The method of embodiment 4, wherein said disengaging step comprises releasing one end 72 of the thread-like member 70; and pulling on an opposite end 71 of the thread-like member 70.

6. The method of embodiment 5, further comprising: removing the thread-like member 70 from the patient 480.

7. The method of any one of embodiments 1 to 6, wherein the tube portion 28 of the distal end 24 of the tube 20 comprises one or more side holes 28 extending through a sidewall 201 of the tube 20; and the thread-like member 70 comprises thread or string 70 with a length of from about 20 to about 80 centimeters (cm), and a size so as to enable the thread or string 70 to extend through the one or more side holes 28.

8. The method of any one of embodiments 1 to 7, wherein the tube 20 comprises a feeding tube 20.

9. The method of any one of embodiments 1 to 8, wherein the tube 20 has an overall length $L_c$ ranging from about 100 to about 150 cm.

10. The method of any one of embodiments 1 to 9, further comprising: delivering one or more nutrients to the patient 480 through one or more openings 266 or side holes 28 within the tube 20.

11. The method of claim 10, wherein the one or more nutrients are introduced into the duodenum 460 of the patient 480, said method comprising: guiding the tube 20 into the patient's stomach 380 until an inflatable balloon component 282 of the tube 20 passes through a pyloric sphincter 450; and inflating the inflatable balloon component 282 of the tube 20 so as to allow natural peristalsis of the patient 480 to further advance the tube 20 comprising an inflated balloon component into the patient's duodenum 460/470.

12. The method of embodiment 11, wherein said inflating step comprises inflating the inflatable balloon component 282 with water 91.

13. The method of embodiment 12, wherein said inflating step further comprises closing a valve 205 to prevent the water 91 from exiting the inflatable balloon component 282.

14. The method of any one of embodiments 1 to 13, wherein said method further comprises: conducting an x-ray procedure so as to verify a position of the tube 20 within the patient 480.

15. The method of any one of embodiments 1 to 14, further comprising: removing the tube 20 from the patient 480.

Kits for Inserting a Tube Through the Nasopharynx of a Patient

16. A kit for inserting a tube 20 through a nasopharynx 481 of a patient 480 using the method of any one of embodiments 1 to 15, said kit comprising the tube 20 sized so as to move through a nasopharynx 481 of a patient 480; and a thread-like member 70 that is attachable to a tube portion 28 of a distal end 24 of the tube 20 and can be tensioned so as to alter an initial direction A of the distal end 24 of the tube 20 and point the distal end 24 of the tube 20 towards a throat 483 of the patient 480.

17. A kit for inserting a tube 20 through the nasopharynx 481 of a patient 480, said kit comprising: a tube 20 sized so as to move through a nasopharynx 481 of a patient 480; and a thread-like member 70 that is attachable to a tube portion 28 of a distal end 24 of the tube 20 and can be tensioned so as to alter an initial direction A of the distal end 24 of the tube 20 and point the distal end 24 of the tube 20 towards a throat 483 of the patient 480.

18. The kit of embodiment 16 or 17, wherein the tube portion 28 of the distal end 24 of the tube 20 comprises one or more side holes 28 extending through a sidewall 201 of the tube 20.

19. The kit of any one of embodiments 16 to 18, wherein the tube 20 of the kit comprises a feeding tube 20.

20. The kit of any one of embodiments 16 to 19, wherein the tube 20 comprises a tube 20 suitable for use with a removable stylet 30, said tube 20 comprising a proximal end 22, a distal end 24 opposite said proximal end 22, a tube channel 26 extending along a length $L_c$ of said tube 20 from said proximal end 22 towards said distal end 24, and an inflatable balloon component 282 positioned along said tube 20 proximate said distal end 24.

21. The kit of embodiment 20, wherein said tube channel 26 extends less than a complete length of said tube 20.

22. The kit of embodiment 20, wherein said tube channel 26 extends a complete length of tube 20.

23. The kit of any one of embodiments 16 to 22, wherein said distal end 24 comprises a distal end tip 25, and said distal end tip 25 is open (e.g., as shown in FIGS. 6A-6B). Note, in other embodiments, the distal end tip 25 may be closed (e.g., as shown in FIGS. 5A-5B).

24. The kit of any one of embodiments 20 to 23, wherein said inflatable balloon component 282 is positioned a distance $d_b$ from a distal end tip 25 of said tube 20.

25. The kit of any one of embodiments 20 to 24, wherein said inflatable balloon component 282 is positioned a distance $d_b$ of from about 1.0 centimeter (cm) to about 10.0 cm from a distal end tip 25 of said tube 20 (or any other distance $d_b$ from the distal end tip 25 of said tube 20 from greater than about 0.5 cm to about 10 cm, in increments of 0.1 cm, or any range of distances $d_b$ between about 1.0 cm and about 10 cm, in increments of 0.1 cm, e.g., from about 1.0 to about 2.0 cm, with 1.5 cm being a preferred distance $d_b$ in some embodiments).

26. The kit of any one of embodiments 20 to 25, wherein said inflatable balloon component 282 extends along an outer surface 27 of said tube 20. Inflatable balloon component 282 may be attached to outer surface 27 of tube 20 via any known attaching member (not shown). Suitable attaching members include, but are not limited to, an adhesive, and a mechanical bond (e.g., an ultrasonic welding bond).

27. The kit of any one of embodiments 20 to 26, wherein said inflatable balloon component 282 is sized so as to contain up to 20 milliliters (ml) of inflating fluid 91 (see, FIG. 8) (or any amount up to 20 ml, or any range between greater than 0 ml to about 20 ml, in increments of 0.1 ml, with about 3.0 ml being preferred for adult patients, and about 1.0 ml being preferred for smaller, pediatric patient).

28. The kit of any one of embodiments 20 to 27, wherein said inflatable balloon component 282 is sized so as to contain from about 1.0 ml to about 5.0 ml of inflating fluid 91.

29. The kit of any one of embodiments 20 to 28, wherein said inflatable balloon component 282 contains from about 1.0 ml to about 5.0 ml of inflating fluid 91.

30. The kit of any one of embodiments 27 to 29, wherein said inflating fluid 91 comprises water. It should be noted that, in other embodiments, the inflating fluid 91 may comprise another type of fluid, such as air.

31. The kit of any one of embodiments 16 to 30, wherein said tube 20 further comprises one or more inflating holes 29 with each inflating hole 29 having an inflating hole outlet 291 along an outer surface 27 of said tube 20 positioned underneath said inflatable balloon component 282. Typically, the tube 20 of the present invention comprise a single inflating hole 29 or up to about four inflating holes 29.

32. The kit of any one of embodiments 16 to 31, wherein said tube 20 further comprises one or more inflating channels 29' extending along a length $L_c$ of said tube 20 and within a sidewall 201 of said tube 20, each of said one or more inflating channels 29' comprising an inflating channel inlet opening 292 proximate said proximal end 22 and an inflating channel outlet opening 291 along an outer surface 27 of said tube 20 positioned underneath said inflatable balloon component 282. Typically, the tube 20 of the present invention comprise a single inflating channel 29' or up to about four inflating channels 29'.

33. The kit of any one of embodiments 16 to 32, wherein said tube 20 further comprises one or more inflation tubes 202 attached to said tube 20 along an outer surface 27 of said tube 20 proximate said tube proximal end 22. Typically, the one or more inflation tubes 202 are attached to the tube 20 along an outer surface 27 of said tube 20 as shown in FIG. 9. Each inflation tube 202 may be attached to tube 20 along outer surface 27 via any known attaching member (not shown). Suitable attaching members include, but are not limited to, an adhesive, and a mechanical bond (e.g., an ultrasonic welding bond). Typically, the tubes 20 of the present invention comprise a single inflation tube 202, even though the tubes 20 of the present invention may comprise more than one inflation tube 202.

34. The kit of embodiment 33, further comprising one or more pilot balloons 203 positioned along and in fluid communication with said single inflation tube 202, pilot balloon 203 being positioned so as to indicate whether said inflatable balloon component 282 is inflated or deflated.

35. The kit of embodiment 33 or 34, further comprising one or more inflating devices 288 operatively adapted to provide inflating fluid 91 through said one or more inflation tubes 202 and into said inflatable balloon component 282. Typically, the tubes 20 of the present invention comprise a single inflating device 288, even though the tubes 20 of the present invention may comprise more than one inflating device 288.

36. The kit of embodiment 35, wherein said one or more inflating devices 288 comprise a syringe 288 (see, FIG. 11). (The syringe 288 may be connected to inflation tube 202 at port/valve 205 as shown in FIG. 5A so as to input water or another fluid into inflation tube 202.)

37. The kit of any one of embodiments 16 to 36, wherein said tube 20 further comprises one or more valves 205 that temporarily prevent inflating fluid 91 from exiting said inflatable balloon component 282 once inflated. Typically, the tubes 20 of the present invention comprise a single valve 205 for the tube 20 or a single valve 205 for each inflation tube 202. Each valve 205 may comprise a one-way valve that allow fluid flow in a single direction (i.e., fluid flow into inflatable balloon component 282) or a two-way valve that allow fluid flow in two directions (i.e., fluid flow into and out of inflatable balloon component 282). Although valve 205 is shown in FIG. 5A at an end 206 of inflation tube 202, it should be understood that one or more valves 205 may be positioned at any location along the length of inflation tube 202.

38. The kit of any one of embodiments 20 to 37, wherein said tube 20 further comprises one or more valves 205 that temporarily prevent inflating fluid 91 from exiting said inflatable balloon component 282 once inflated, said one or more valves 205 being positioned along said one or more inflation tubes 202. As discussed above, in some embodiments, the tubes 20 of the present invention comprise a single valve 205 along each inflation tube 202.

39. The kit of any one of embodiments 16 to 38, wherein said tube 20 further comprises one or more visual markers 208 extending along an outer surface 27 of said tube 20, each of said one or more visual markers 208 providing a visual indication of a tube length extending from a tube distal end tip 25 to a given visual marker 208. In other words, the visual markers provide a visual reference that indicates a position (i.e., distance) of the tube distal end tip 25 of the feeding tube 10 within a patient 480.

40. The kit of any one of embodiments 16 to 39, wherein said tube 20 further comprises two or more sets of one or more visual markers 208 (e.g., sets 208*a*, 208*b* and 208*c* shown in FIG. 5A) extending along an outer surface 27 of said tube 20, each of said one or more visual markers 208 providing a visual indication of a tube length extending from a tube distal end tip 25 to a given visual marker.

41. The kit of embodiment 40, wherein said two or more sets of one or more visual markers 208 comprise (i) a single visual marker 208*a* at a distance of about 50 cm from a tube distal end tip 25, (ii) two adjacent visual markers 208*b* at a distance of about 80 cm from said tube distal end tip 25, and (iii) three adjacent visual markers 208*c* at a distance of about 110 cm from said tube distal end tip 25. For example, the 50 cm mark 208*a* may correspond to a lower end of the patient's esophagus, the 80 cm mark 208*b* may correspond to the first part of the patient's duodenum, and the 110 cm mark 208*c* may correspond to the tube distal tip 25 being within the 4$^{th}$ part of the patient's duodenum in an adult size patient.

42. The kit of any one of embodiments 18 to 41, wherein each side hole 28 (1) extends from an inner surface 261 of said tube 20 along said tube channel 26 to an outer surface 27 of said tube 20, and (2) is positioned (i) between said inflatable balloon component 282 and a tube distal end tip 25, (ii) between said inflatable balloon component 282 and said tube proximal end 22, or (iii) both (i) and (ii). Typically, the tubes 20 of the present invention comprise two or more side holes 28, more typically, from about 1 to about 4 side holes 28. See, for example, side holes 28 shown in FIGS. 5A-6B.

43. The kit of embodiment 42, wherein at least one of said side holes 28 is positioned between said inflatable balloon component 282 and a tube distal end tip 25.

44. The kit of any one of embodiments 16 to 43, wherein said tube 20 further comprises a feeding tube hub 80 positioned at said tube proximal end 22, said feeding tube hub 80 comprising one or more hub ports 82 to allow for aspiration or delivery of medications via said tube 20.

45. The kit of any one of embodiments 16 to 44, wherein said tube 20 further comprises a feeding tube hub 80 positioned at said tube proximal end 22, said feeding tube hub 80 comprising two or more hub ports 82 to allow for aspiration or delivery of medications via said tube 20. Typically, the tubes 20 of the present invention comprise two to three hub ports 82.

46. The kit of any one of embodiments 16 to 45, wherein a wall 201 of said tube 20 (see, FIG. 9) extending along a length $L_c$ of said tube 20 comprises an MRI compatible reinforcing material 222. In some embodiments, the MRI compatible reinforcing material 222 comprising a coil reinforcing material 222 extending along a length of said tube 20 and within or along an inner portion of said wall 201 with individual coils of said coil reinforcing material 222 extending substantially perpendicular to length $L_c$ of tube 20 (see, FIGS. 7-9).

47. The kit of any one of embodiments 16 to 46, wherein a wall 201 of said tube 20 extending along a length $L_c$ of said tube 20 comprises medical grade radio-opaque material. Suitable medical grade radio-opaque materials include, but are not limited to, polyvinyl chloride (PVC), and polyurethane loaded with from about 20 wt % to about 40 wt % barium sulfate or bismuth subsalicylate.

48. The kit of any one of embodiments 16 to 47, further comprising a removable stylet 30, said removable stylet 30 comprising a stylet proximal end 31 and a stylet distal end 34 opposite said stylet proximal end 31, said stylet distal end 34 being sized so as to be insertable within (i) a tube opening 23 at said tube proximal end 22, and (ii) said tube channel 26. Suitable removable stylets and removable stylet components/features are disclosed in U.S. Pat. No. 9,713,578 (Gabriel), the subject matter of which is hereby incorporated by reference in its entirety.

49. The kit of embodiment 48, wherein said removable stylet 30 comprises a stylet hub 90 at said stylet proximal end 31.

50. The kit of any one of embodiments 16 to 49, wherein the thread-like member 70 comprises thread or string with a length of from about 20 to about 80 centimeters (cm), and a size so as to enable the thread or string to extend through one or more side holes 28, when present, of said tube 20.

Methods of Making Kits

51. A method of making the kit of any one of embodiments 16 to 50, said method comprising: combining (i) a tube 20 sized so as to move through a nasopharynx 481 of a patient 480; and (ii) a thread-like member 70 that is attachable to a tube portion 28 of a distal end 24 of the tube 20 and can be tensioned so as to alter an initial direction A of the distal end 24 of the tube 20 and point the distal end 24 of the tube 20 towards a throat 483 of the patient 480.

It should be understood that although the above-described kits and methods are described as "comprising" one or more components or steps, the above-described kits and methods may "comprise," "consists of," or "consist essentially of" any of the above-described components or steps of the kits and methods. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a kit and/or method that "comprises" a list of elements (e.g., components or steps) is not necessarily limited to only those elements (or components or steps), but may include other elements (or components or steps) not expressly listed or inherent to the kit and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a kit and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Further, it should be understood that the herein-described kits and methods may comprise, consist essentially of, or consist of any of the herein-described components, steps and features, as shown in the figures with or without any feature(s) not shown in the figures. In other words, in some embodiments, the kits and/or methods of the present invention do not have any additional features other than those shown in the figures, and such additional features, not shown in the figures, are specifically excluded from the kits and/or methods. In other embodiments, the kits and/or methods of the present invention do have one or more additional features that are not shown in the figures.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Kits and methods as described in embodiments 1 to 51 and shown in FIGS. 2A-12C were prepared and utilized.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of inserting a tube through a nasopharynx of a patient, said method comprising:

inserting the tube through a naris of the patient, the tube comprising one or more side holes extending through a sidewall of the tube at a distal end of the tube;

when the distal end of the tube is proximate a rear surface of the nasopharynx, pulling on or holding in place a thread-like member that extends through the one or more side holes of the tube so as to alter an initial direction of the distal end of the tube and point the distal end of the tube towards a throat of the patient;

disengaging the thread-like member from the tube; and further advancing the distal end of the tube toward the throat of the patient without the thread-like member.

2. The method of claim 1, further comprising:

prior to said disengaging step, advancing the distal end of the tube toward the throat of the patient while pulling on or holding in place the thread-like member.

3. The method of claim 1, further comprising:

prior to said disengaging step, advancing the distal end of the tube toward the throat of the patient while holding in place the thread-like member.

4. The method of claim 1, wherein said disengaging step comprises:

releasing one end of the thread-like member; and pulling on an opposite end of the thread-like member.

5. The method of claim 4, further comprising:

removing the thread-like member from the patient.

6. The method of claim 5, further comprising:

after said removing step, removing the tube from the patient.

7. The method of claim 1, wherein the thread-like member comprises thread or string with a length of from about 20 centimeters to about 80 centimeters.

8. The method of claim 1, wherein the tube comprises a feeding tube.

9. The method of claim 1, wherein the tube has an overall length ranging from about 100 centimeters to about 150 cm.

10. The method of claim 1, further comprising:

delivering one or more nutrients to the patient through one or more openings or the one or more side holes within the tube.

11. The method of claim 10, further comprising:

removing the tube from the patient.

12. The method of claim 1, wherein said pulling on or holding in place step comprises pulling on or holding in place opposite ends of the thread-like member that extends through the one or more side holes of the tube.

13. The method of claim 1, further comprising:

prior to said inserting step, threading one end of the thread-like member through the one or more side holes of the tube.

14. A method of inserting a feeding tube through a nasopharynx of a patient, said method comprising:

inserting the feeding tube through a naris of the patient, the feeding tube comprising one or more side holes extending through a sidewall of the feeding tube at a distal end of the feeding tube;

when the distal end of the feeding tube is proximate a rear surface of the nasopharynx, pulling on or holding in place opposite ends of a thread or the string that extends through the one or more side holes of the feeding tube so as to alter an initial direction of the distal end of the feeding tube and point the distal end of the feeding tube towards a throat of the patient;

advancing the distal end of the feeding tube toward the throat of the patient while pulling on or holding in place the thread or the string;

disengaging the thread or the string from the feeding tube;

removing the thread or the string from the patient; and further advancing the distal end of the feeding tube toward the throat of the patient without the thread or the string;

wherein said disengaging step comprises:

releasing one of the ends of the thread or the string; and pulling on another of the ends of the thread or the string.

15. The method of claim 14, further comprising:

prior to said inserting step, threading one of the ends of the thread or the string through the one or more side holes of the feeding tube.

* * * * *